United States Patent [19]

Foo et al.

[11] Patent Number: 6,120,700
[45] Date of Patent: *Sep. 19, 2000

[54] HYDROCYANATION OF DIOLEFINS AND ISOMERIZATION OF NONCONJUGATED 2-ALKYL-3-MONOALKENENITRILES

[75] Inventors: Thomas Foo; James Michael Garner, both of Wilmington, Del.; Wilson Tam, Boothwyn, Pa.

[73] Assignee: E. I. du Pont de Nemours and Company, Wilmington, Del.

[ * ] Notice: This patent issued on a continued prosecution application filed under 37 CFR 1.53(d), and is subject to the twenty year patent term provisions of 35 U.S.C. 154(a)(2).

[21] Appl. No.: 09/373,492

[22] Filed: Aug. 12, 1999

Related U.S. Application Data

[62] Division of application No. 09/121,104, Jul. 23, 1998, Pat. No. 5,981,772.
[60] Provisional application No. 60/054,023, Jul. 29, 1997.
[51] Int. Cl.[7] .................................................. C09K 3/00
[52] U.S. Cl. ..................... 252/182.3; 549/348; 558/78; 558/156
[58] Field of Search .................. 252/182.3; 549/348; 558/78, 156

[56] References Cited

U.S. PATENT DOCUMENTS

| 3,496,215 | 2/1970 | Drinkard et al. ................. 260/465.8 |
|---|---|---|
| 3,496,217 | 2/1970 | Drinkard, Jr. et al. ............. 260/465.8 |
| 3,536,748 | 10/1970 | Drinkard, Jr. et al. ............. 260/465.9 |
| 3,676,481 | 7/1972 | Chia .................................... 260/465.9 |
| 5,512,696 | 4/1996 | Kreutzer et al. ..................... 558/338 |
| 5,821,378 | 10/1998 | Foo et al. ............................ 558/338 |
| 5,910,600 | 6/1999 | Urata et al. ......................... 558/162 |

FOREIGN PATENT DOCUMENTS

| WO 95/14659 | 6/1995 | WIPO . |
| WO 96/16022 | 5/1996 | WIPO . |
| WO 96/22968 | 8/1996 | WIPO . |

OTHER PUBLICATIONS

Baker et al., *J. Chem. Soc., Chem. Commun.*, 803–804, 1991.

*Primary Examiner*—Johann Richter
*Assistant Examiner*—Joseph Murray

[57] ABSTRACT

Improved liquid phase process useful in the hydrocyanation of diolefinic compounds to produce nonconjugated acyclic nitriles and to the liquid phase process of isomerization of the nitrites to, among other things, 3- and/or 4-monoalkene linear nitriles. The improvement involves conducting the process in the presence of zero-valent nickel and a multidentate phosphite ligand. Novel multidentate phosphite ligands and catalyst precursor compositions made therefrom are also disclosed.

2 Claims, No Drawings

HYDROCYANATION OF DIOLEFINS AND ISOMERIZATION OF NONCONJUGATED 2-ALKYL-3-MONOALKENENITRILES

This is a division of application Ser. No. 09/121,104 filed Jul. 23, 1998, now U.S. Pat. No. 5,981,772 Nov. 9, 1999, which stemmed from Provisional application No. 60/054,023, filed Jul. 29, 1997.

FIELD OF THE INVENTION

This invention generally relates to an improved liquid phase process useful in the hydrocyanation of diolefinic compounds to produce nonconjugated acyclic nitriles and to a liquid phase process of isomerization of said nitriles to, among other things, 3- and/or 4-monoalkene linear nitrites. The improvement resides in conducting the processes in the presence of zero-valent nickel and a multidentate phosphite ligand.

BACKGROUND OF THE INVENTION

Catalytic hydrocyanation systems, particularly pertaining to the hydrocyanation of olefins, are known in the art. For example, liquid phase systems useful for the hydrocyanation of butadiene to form pentenenitriles (PN) are known in the art. For example, Drinkard, U.S. Pat. No. 3,496,215, discloses the hydrocyanation of butadiene using nickel catalysts with monodentate phosphite ligands. As used in this patent, and as will be used herein, the term "pentenenitrile" is intended to mean cyanobutene. Likewise, "butenenitrile" means cyanopropene. Bidentate phosphite ligands complexed to zero-valent nickel and platinum are known to be useful in the liquid phase hydrocyanation of butadiene, as described by Baker et al., *J Chem. Soc., Chem. Commun.,* 1991, 803–804.

The pentenenitriles so formed are subjected to further hydrocyanation and/or isomerization to form adiponitrile (ADN), a commercially important material in the manufacture of nylon. For example, Drinkard, U.S. Pat. No. 3,536,748, discloses the liquid phase isomerization of 2-methyl-3-butenenitrile in the presence of a zero valent nickel complex and Chia, U.S. Pat. No. 3,676,481, discloses an improvement additionally utilizing tri(hydrocarbyl)boron promoters.

The hydrocyanation of activated olefins such as conjugated olefins (e.g., butadiene and styrene) and strained olefins (e.g., norbornene) proceeds without the use of a Lewis acid promoter, while hydrocyanation of unactivated olefins such as 1-octene and 3-pentenenitrile normally require the use of a Lewis acid promoter. Teachings regarding the use of a promoter in the hydrocyanation reaction appear, for example, in U.S. Pat. No. 3,496,217.

Certain multidentate phosphite ligands useful in the present invention for the hydrocyanation of diolefins have been used for the hydrocyanation of monoolefins. Commonly assigned, WO 95/14659 and U.S. Pat. No. 5,512,696, disclose bidentate phosphite ligands preferably used in combination with a Lewis acid promotor to hydrocyanate monoolefins.

The present invention provides for an improved process for the hydrocyanation of diolefinic compounds, such as butadiene, and isomerization of nonconjugated acyclic nitrites without the need for Lewis acid promoters utilizing zero-valent nickel and a multidentate phosphite ligand. Other objects and advantages of the present invention will become apparent to those skilled in the art upon reference to the detailed description of the invention which hereinafter follows.

SUMMARY OF THE INVENTION

The present invention provides an improved process for the liquid phase hydrocyanation of diolefinic compounds and isomerization of the resulting nonconjugated acyclic nitrites comprising, reacting an acyclic aliphatic diolefinic compound, preferably butadiene, with a source of HCN, wherein the improvement comprises conducting the hydrocyanation and/or isomerzation in the presence of a catalyst precursor composition comprising zero-valent nickel and at least one multidentate phosphite ligand selected from the group consisting of compounds represented by Formulas I, II, III, IV, V, VI, VII, VIII, IX, X, XI, XII, XIII and XIV as set forth below:

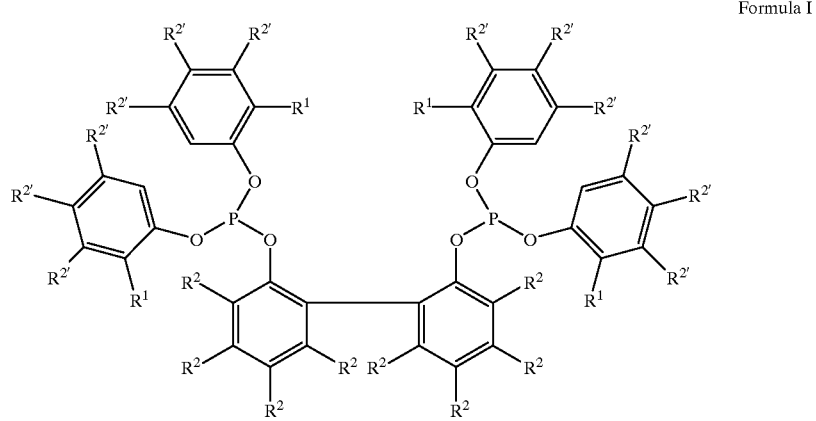

Formula I

Formula II
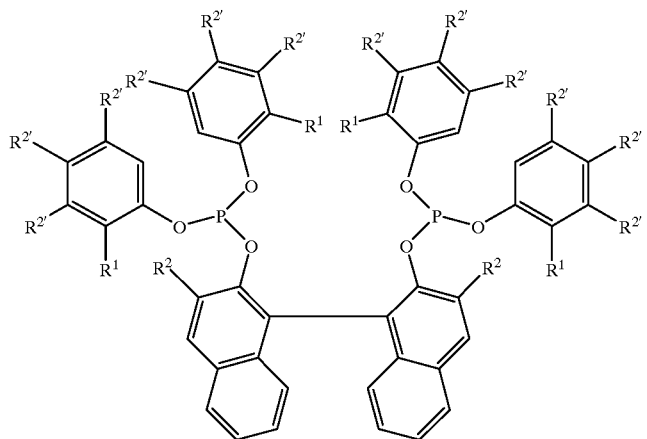
Formula III
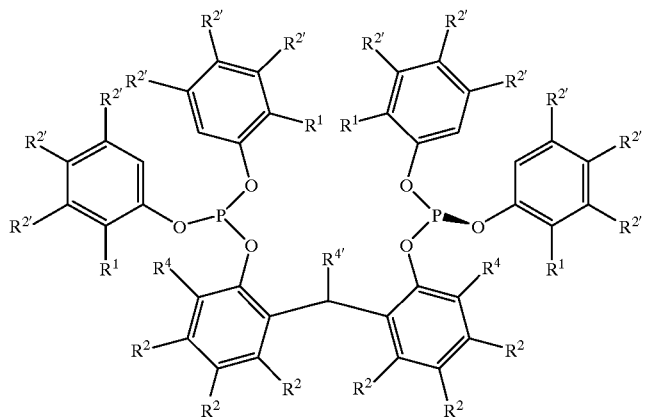
Formula IV
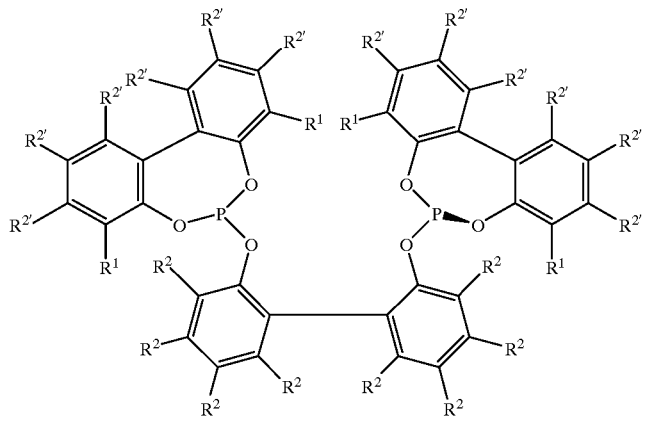

Formula V
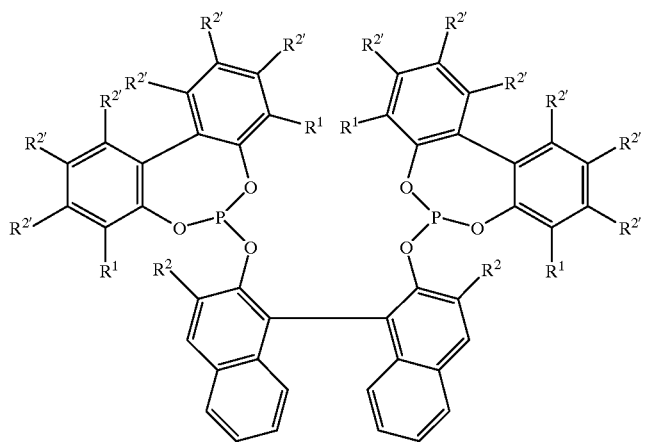
Formula VI
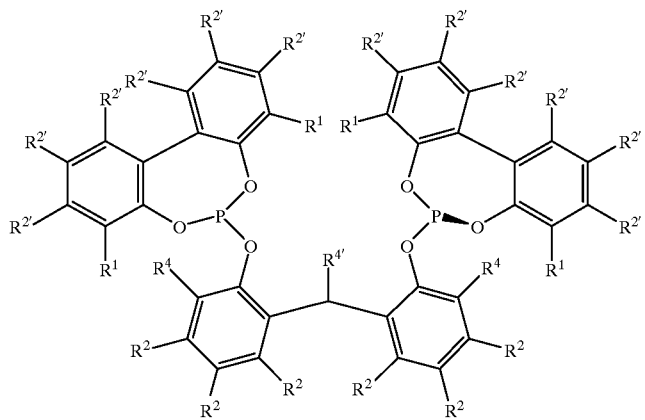
Formula VII
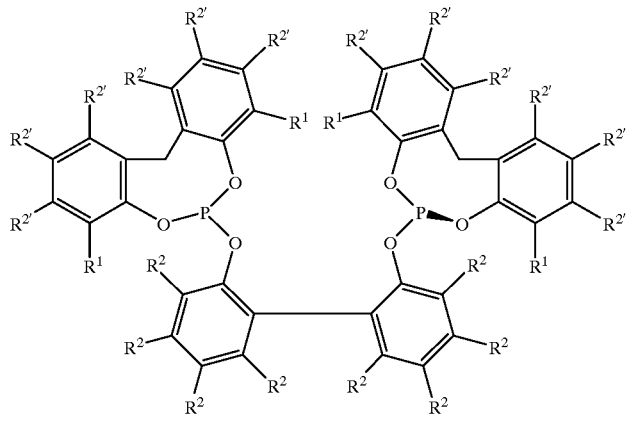

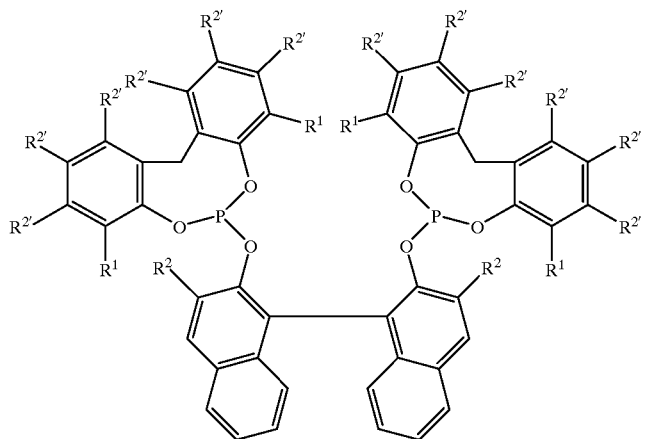
Formula VIII
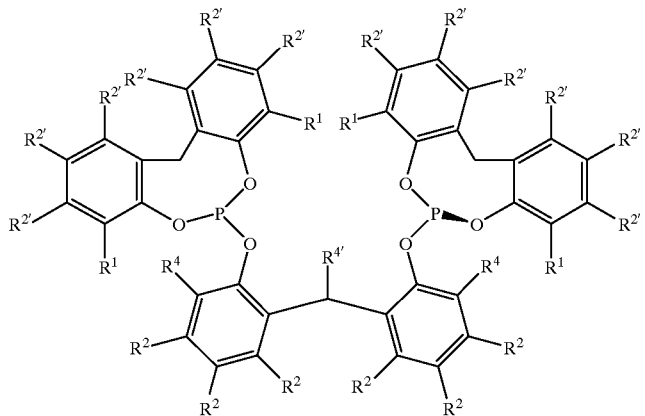
Formula IX
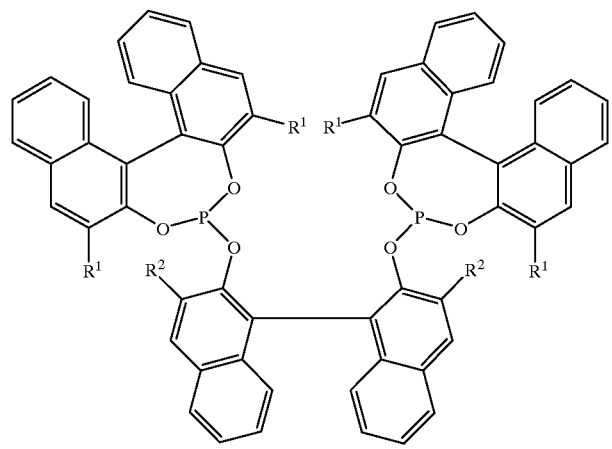
Formula X

Formula XI
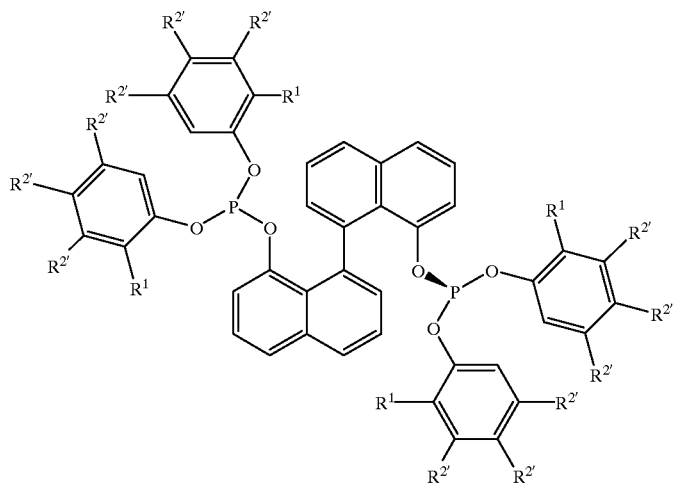
Formula XII
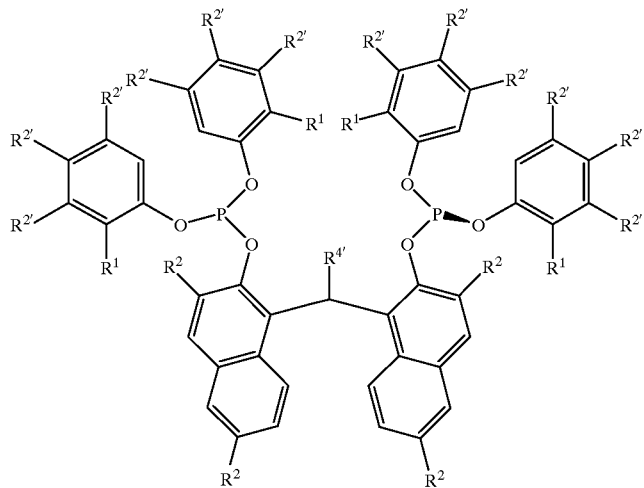
Formula XIII
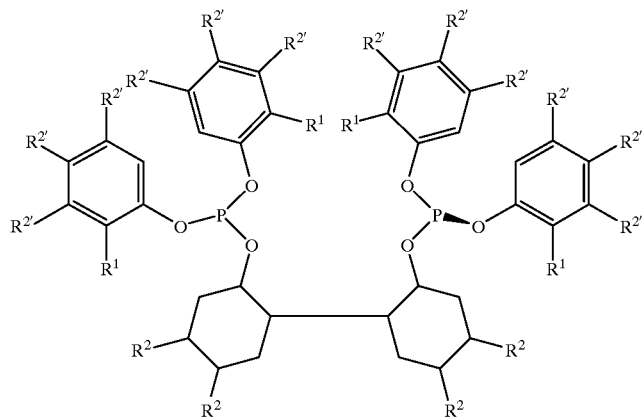

-continued

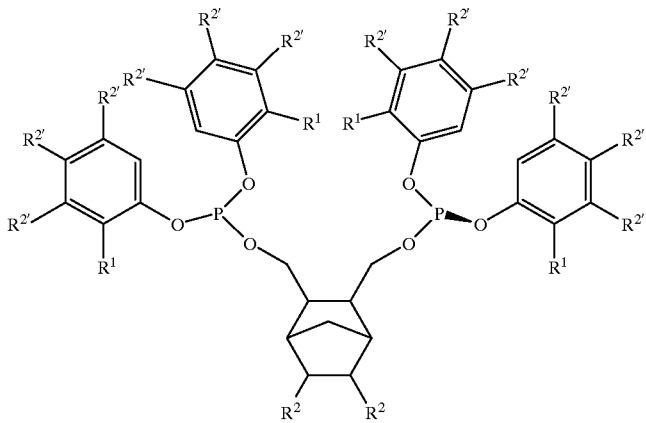

Formula XIV wherein
- each $R^1$ is independently a primary, secondary, or tertiary hydrocarbyl of 1 to 12 carbon atoms or $CH_2OR^3$ wherein $R^3$ is a $C_1$ to $C_{12}$ alkyl; with the proviso that at least one of $R^1$ must be a primary hydrocarbyl or $CH_2OR^3$;
- each $R^2$ is independently H, halogen, primary or secondary hydrocarbyl of 1 to 12 carbon atoms, $OR^3$ wherein $R^3$ is a $C_1$ to $C_{12}$ alkyl, or $CO_2R^{3'}$ wherein $R^{3'}$ is an aryl or a $C_1$ to $C_{12}$ alkyl;
- each $R^{2'}$ is independently H, halogen, CHO, primary, secondary or tertiary hydrocarbyl of 1 to 12 carbon atoms, $OR^3$ wherein $R^3$ is a $C_1$ to $C_{12}$ alkyl, $CO_2R^{3'}$ wherein $R^{3'}$ is an aryl or a $C_1$ to $C_{12}$ alkyl, or $C(R^3)(O)$ wherein $R^3$ is a $C_1$ to $C_{12}$ alkyl;
- each $R^4$ is independently H, a primary or secondary hydrocarbyl of 1 to 12 carbon atoms or $CO_2R^3$ wherein $R^3$ is a $C_1$ to $C_{12}$ alkyl; and
- each $R^{4'}$ is independently H, a primary or secondary hydrocarbyl of 1 to 12 carbon atoms or aryl.

The present invention provides an improved process for the liquid phase hydrocyanation of diolefinic compounds, reacting an acyclic aliphatic diolefinic compound, preferably butadiene, with a source of HCN, wherein the improvement comprises conducting the hydrocyanation in the presence of a catalyst precursor composition comprising zero-valent nickel and at least one multidentate phosphite ligand selected from the group consisting of compounds represented by Formulas I, II, III, IV, V, VI, VII, VIII, IX, X, XI, XII, XIII and XIV as set forth below:

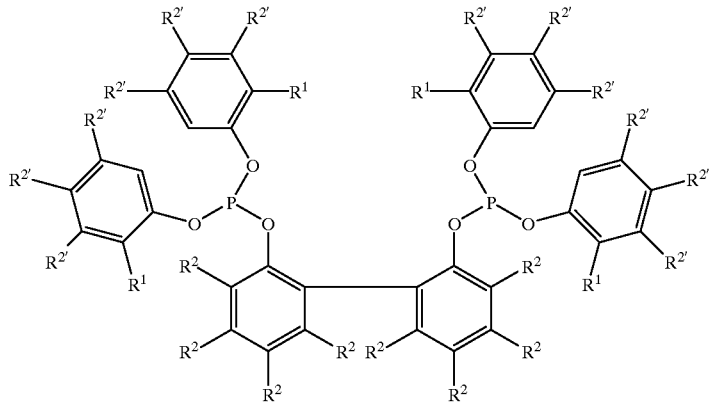

Formula I

-continued
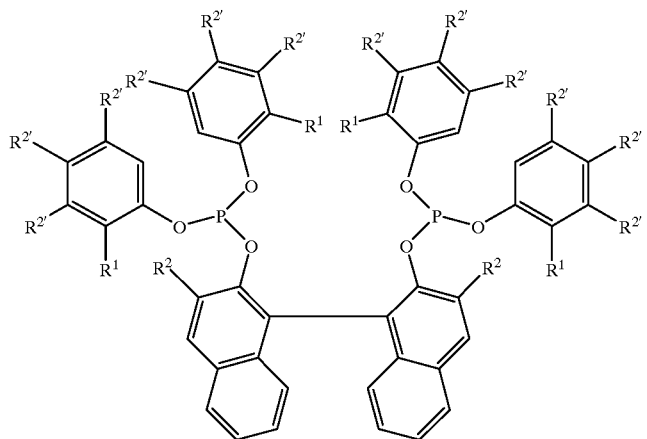
Formula II
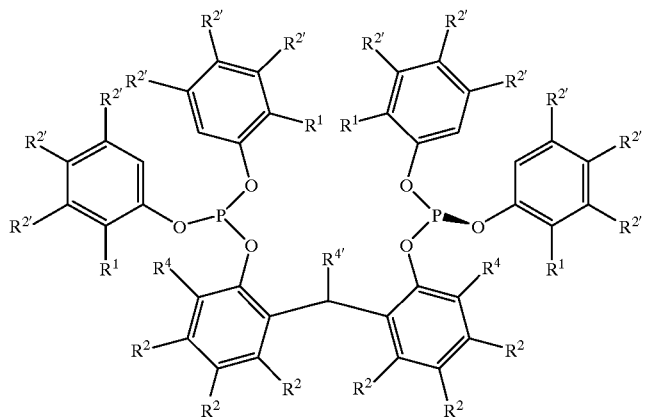
Formula III
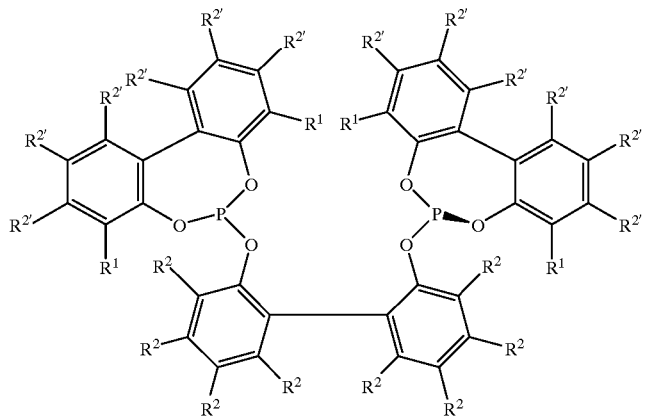
Formula IV

-continued
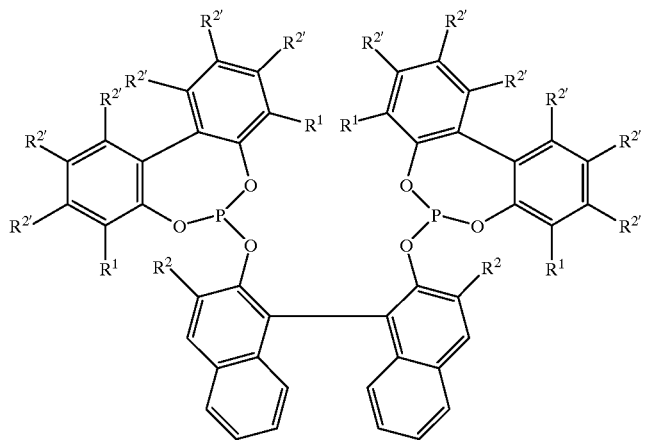
Formula V
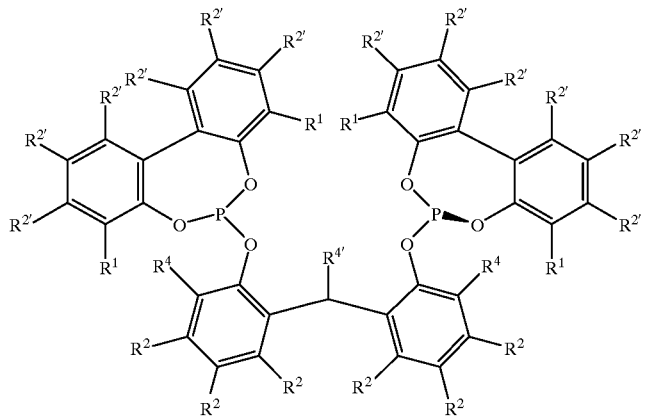
Formula VI
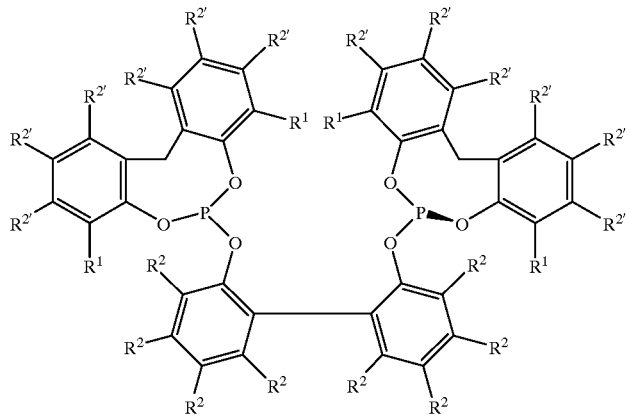
Formula VII

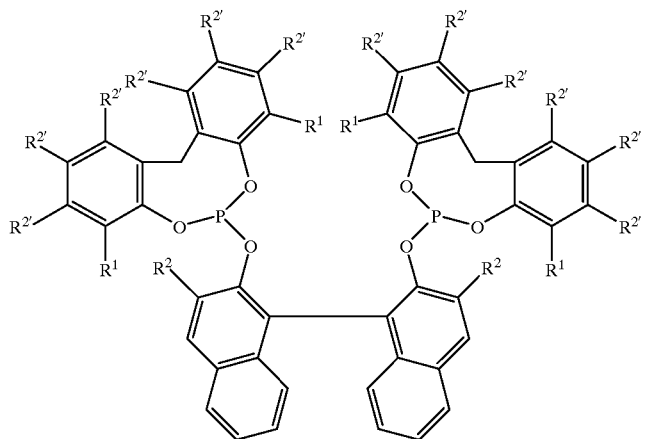
Formula VIII
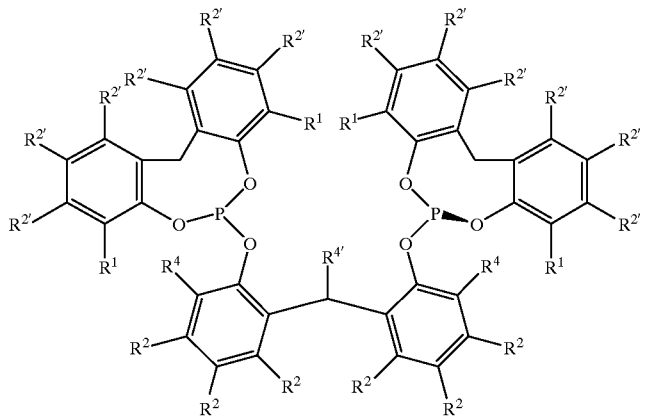
Formula IX
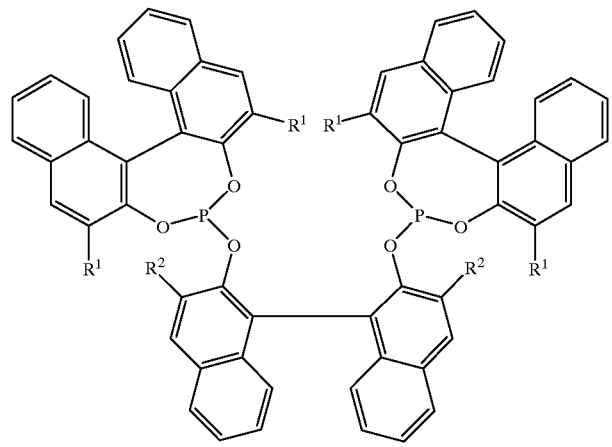
Formula X

-continued
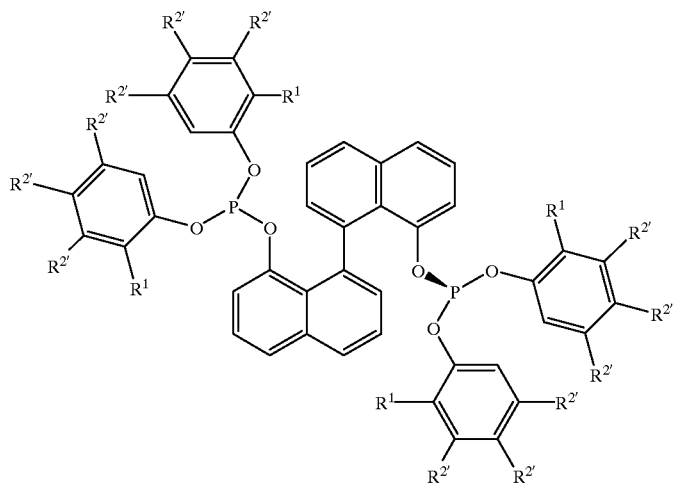
Formula XI
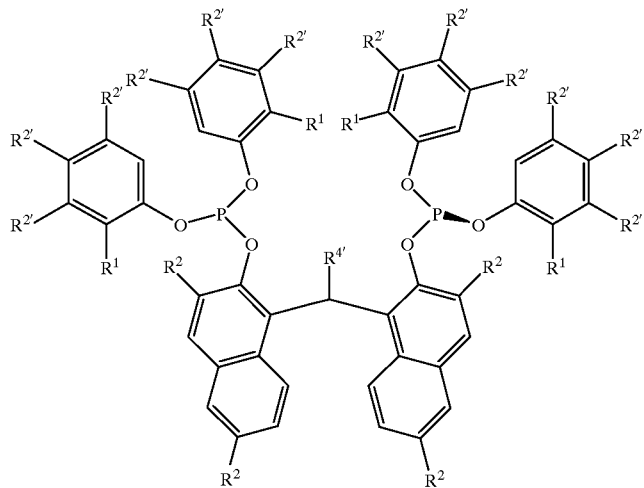
Formula XII
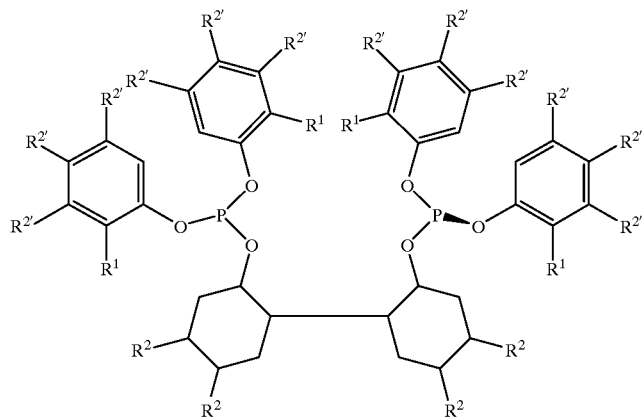
Formula XIII

-continued

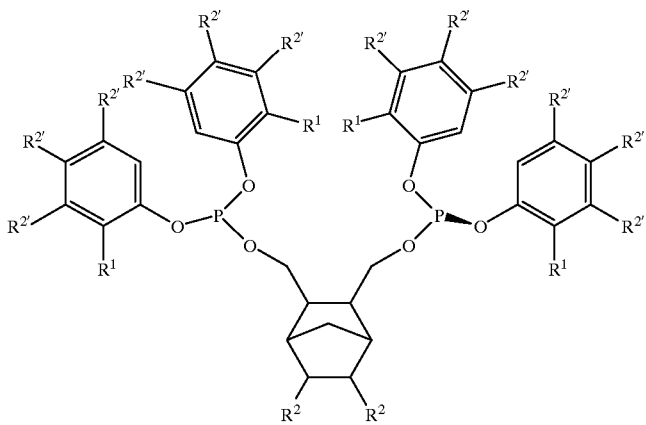

Formula XIV wherein
- each $R^1$ is independently a primary, secondary, or tertiary hydrocarbyl of 1 to 12 carbon atoms or $CH_2OR^3$ wherein $R^3$ is a $C_1$ to $C_{12}$ alkyl; with the proviso that at least one of $R^1$ must be a primary hydrocarbyl or $CH_2OR^3$;
- each $R^2$ is independently H, halogen, primary or secondary hydrocarbyl of 1 to 12 carbon atoms, $OR^3$ wherein $R^3$ is a $C_1$ to $C_{12}$ alkyl, or $CO_2R^{3'}$ wherein $R^{3'}$ is an aryl or a $C_1$ to $C_{12}$ alkyl;
- each $R^{2'}$ is independently H, halogen, CHO, primary, secondary or tertiary hydrocarbyl of 1 to 12 carbon atoms, $OR^3$ wherein $R^3$ is a $C_1$ to $C_{12}$ alkyl, $CO_2R^{3'}$ wherein $R^{3'}$ is an aryl or a $C_1$ to $C_{12}$ alkyl, or $C(R^3)(O)$ wherein $R^3$ is a $C_1$ to $C_{12}$ alkyl;
- each $R^4$ is independently H, a primary or secondary hydrocarbyl of 1 to 12 carbon atoms or $CO_2R^3$ wherein $R^3$ is a $C_1$ to $C_{12}$ alkyl; and
- each $R^{4'}$ is independently H, a primary or secondary hydrocarbyl of 1 to 12 carbon atoms or aryl.

The reactions are most conveniently performed continuously from hydrocyanation of the starting diolefin to the final 3- and/or 4-monoalkene linear nitriles. However, the processes can be conducted stepwise, i.e., the nonconjugated acyclic nitriles resulting from the hydrocyanation can be isolated per se, prior to isomerization. Furthermore, non-conjugated acyclic nitriles prepared by any method can be used as starting materials for the isomerization in accordance with this invention.

The invention also provides for certain multidentate phosphite ligands according to formulas X–XIV and catalyst precursor compositions made therefrom.

DETAILED DESCRIPTION OF THE PREFERRED EMBODIMENTS

The catalyst precursor compositions useful in the processes of this invention are comprised of a muitidentate phosphite ligand and zero-valent nickel.

The catalyst composition is referred to as a "precursor" only to indicate in all likelihood, during the hydrocyanation reaction the structure of the active catalyst composition may in fact be complexed to an olefin.

These ligands may be prepared by a variety of methods known in the art, for example, see descriptions in WO 93,03839, U.S. Pat. No. 4,769,498; U.S. Pat. No. 4,688,651, *J. Amer. Chem. Soc.*, 1993, 115, 2066. The reaction of the phosphorochloridite of o-cresol with 1,1'-binaphthol in the presence of triethylamine gives a ligand according to Formula II.

The phosphorochloridite may be prepared by a variety of methods known in the art, for example, see descriptions in *Polymer*, 1992, 33, 161; *Inorganic Syntheses*, 1966, 8, 68; U.S. Pat. No. 5,210,260; *Z. Anorg. Allg. Chem.*, 1986, 535, 221. With bulky ortho-substituted phenols (e.g., 2-t-butylphenol), phosphoro-chloridites can be prepared in situ from $PCl_3$ and the phenol. With less bulky groups, purification by high vacuum distillation is typically necessary. High vacuum distillation is difficult for large scale operations.

An improved process for preparing the phosphorochloridite comprises treatment of N,N-dialkyl diarylphosphoramidite with HCl. $ClP(OMe)_2$ has been prepared in this manner, see *Z. Naturforsch*, 1972, 27B, 1429; phosphorochloridites derived from substituted phenols have been prepared using this procedure as described in copending, commonly assigned, application Ser. No. 08/563,718 filed Nov. 28, 1995. N,N-dialkyl diarylphosphoramidites may be prepared by methods known in the art, for example, see descriptions in *Tetrahedron Letters*, 1993, 34, 6451 and *Aust. J Chem*, 1991, 233.

The zero-valent nickel can be prepared or generated according to techniques known in the art (U.S. Pat. No. 3,496,217; 3,631,191; 3,846,461; 3,847,959; and 3,903,120 which are incorporated herein by reference). Zero-valent nickel compounds that contain ligands which can be displaced by the organophosphorus ligand are a preferred source of zero-valent nickel. Two such preferred zero-valent nickel compounds are $Ni(COD)_2$ (COD is 1,5-cyclooctadiene) and $Ni(P(O\text{-}o\text{-}C_6H_4CH_3)_3)_2(C_2H_4)$, both of which are known in the art. Alternatively, divalent nickel compounds may be combined with a reducing agent, and are then able to serve as suitable sources of zero-valent nickel in the reaction. Suitable divalent nickel compounds include compounds of the formula $NiY_2$ where Y is halide, carboxylate, or acetylacetonate. Suitable reducing agents include metal borohydrides, metal aluminum hydrides, metal alkyls, Zn, Fe, Al, Na, or $H_2$. Elemental nickel, preferably nickel powder, when combined with a halogenated catalyst, as described in U.S. Pat. No. 3,903,120, is also a suitable source of zero-valent nickel.

The actual catalyst precursor is a complex of zero-valent nickel with the multidentate phosphite ligand, which is formed when those two materials are combined. An effective catalyst typically requires at least two moles of P atoms for one gram-atom of zero-valent nickel.

The diolefinic compounds reactants used in this invention include primarily conjugated diolefins containing from 4 to 10 carbon atoms; for example, 1,3-butadiene and cis and trans-2,4-hexadienes. Butadiene is especially preferred by reason of its commercial importance in the production of adiponitrile. Other suitable diolefinic compounds include diolefinic compounds substituted with groups which do not deactivate the catalyst, for example, cis and trans-1,3-pentadienes.

The following Formulas XV and XVI illustrate suitable representative starting diolefinic compounds; and Formulas XVII, XVIII, and XIX represent the products obtained from 1,3-butadiene and HCN.

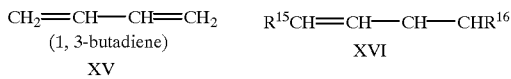

wherein each one of $R^{15}$ and $R^{16}$, independently, is H or a $C_1$ to $C_3$ alkyl.

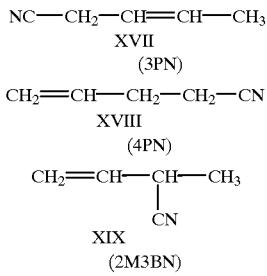

It will be recognized that Compound XV is a special case of Formula XVI, where each one of $R^{15}$ and $R^{16}$ is hydrogen.

In the practice of the hydrocyanation of the diolefin in accordance with the present invention, the following description applies.

The hydrocyanation reaction can be carried out with or without a solvent. The solvent should be a liquid at the reaction temperature and inert towards the unsaturated compound and the catalyst. Generally, such solvents are hydrocarbons such as benzene, xylene, or nitriles such as acetonitrile, benzonitrile, or adiponitrile.

The exact temperature used is dependent, to a certain extent, on the particular catalyst being used, the particular unsaturated compound being used and the desired rate. Generally, temperatures of from −25° C. to 200° C., can be used with from 0° C. to 150° C., being the preferred range.

The reaction may be carried out by charging a reactor with all of the reactants or preferably the reactor is charged with the catalyst or catalyst components, the unsaturated compound and whatever solvent is to be used and the hydrogen cyanide gas is swept over the surface of the reaction mixture or bubbled through said reaction mixture. If desired, when using a gaseous unsaturated organic compound, the hydrogen cyanide and the unsaturated organic compound may be fed together into the reaction medium. The molar ratio of HCN to catalyst generally is varied from about 10:1 to 100,000:1, preferably 100:1 to 5,000:1, for a batch operation. In a continuous operation, such as when using a fixed bed catalyst type of operation, a higher proportion of catalyst may be used such as 5:1 to 100,000:1, preferably 100:1 to 5,000:1, HCN to catalyst.

Preferably, the reaction mixture is agitated, such as by stirring or shaking. The cyanated product can be recovered by conventional techniques such as crystallization of the product from solution or by distillation.

One can either isolate the 2-alkyl-3-monoalkenenitriles produced by the hydrocyanation of the diolefin or proceed continuously with the isomerization under similar reaction conditions.

The 2-alkyl-3-monoalkenenitriles used as the starting materials in the isomerization of this invention can result from the hydrocyanation of diolefin described above or can come from any other available source. The olefinic double bond in the 2-alkyl-3-monoalkenenitriles used as the starting materials in the isomerization of this invention cannot be conjugated to the triple bond of the cyano group. Suitable starting 2-alkyl-3-monoalkenenitriles can also carry groups which do not attack the catalyst, for example, another cyano group. Preferably, the starting 2-alkyl-3-monoalkenenitriles contain from 5 to 8 carbon atoms, excluding any additional substitution. 2-Methyl-3-butenenitrile is especially important in the production of adiponitrile. Other representative nitriles include 2-ethyl-3-butenenitrile and 2-propyl-3-butenenitrile.

The following Formulas XX and XXI illustrate suitable representative starting 2-alkyl-3-monoalkenenitriles. When the staring nitrile is 2-methyl-3-butenenitrile, the isomerization products are those shown in Formulas XXII and XXIII.

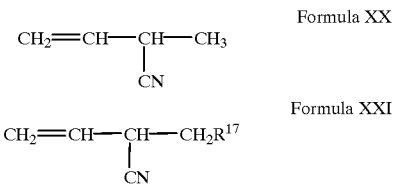

wherein
$R^{17}$ is H or a $C_1$ to $C_3$ alkyl.

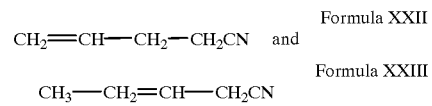

It will be recognized that Formula XX is a special case of Formula XXI, where $R^{17}$ is hydrogen.

The isomerization process of this invention can be carried out, for example, at atmospheric pressure and at any temperature in the range of 10–200° C., preferably in the range 60–150° C. The pressure is not critical, however, and can be above or below atmospheric pressure if desired. Any of the conventional batch or continuous flow procedures may be used either in the liquid phase or in the vapor phase (with respect to the relatively volatile 2-methyl-3-butenenitrile reactant and linear pentenenitrile products). The reactor may be of any mechanically and chemically resistant material, and is usually of glass or an inert metal or alloy, e.g., nickel, copper, silver, gold, platinum, stainless steel, Monel®, Hastelloy®, etc.

The process is usually carried out "neat", i.e., without an added diluent or solvent. Any solvent or diluent that is nondestructive of the catalyst can be used, however. Suitable solvents include aliphatic or aromatic hydrocarbons (hexane, cyclohexane, benzene), ethers (diethyl ether, tetrahydrofuran, dioxane, glycol dimethyl ether, anisole), esters (ethyl acetate, methyl benzoate), nitriles (acetonitrile, benzonitrile), etc.

A nonoxidizing environment is desirable in order to retard oxidative deactivation of the catalyst. Accordingly, an inert atmosphere, e.g., nitrogen, is normally and preferably used, although air may be used if desired at the expense of loss of a proportion of the catalyst through oxidation.

When the process is a typical batch operation in the liquid phase with or without a solvent, the catalytic nickel complex is soluble to some extent at temperatures within the operable range and is usually completely soluble at the most preferred operating temperature. However, the nickel complex is essentially nonvolatile, whereas the 2-methyl-3-butenenitrile reactant and the linear pentenenitrile products are relatively volatile. Accordingly, in a continuous flow procedure the catalyst may be a component of the flowing system in a completely liquid-phase operation, it may be in a mobile nonflowing liquid state in a semi-vapor phase operation, or it may be in a fixed-bed state (usually on a solid support) in a conventional flowing vapor-phase operation.

The time element in the process is not critical, and may generally be governed by practical considerations. The time required for a practical level of conversion of 2-methyl-3-butenenitrile to linear pentenenitriles is dependent upon the temperature of reaction, i.e., operation at lower temperature generally requires a longer time than operation at a higher temperature. A practical reaction time can be in the range of a few seconds to many hours, depending on the particular conditions and method of operation.

The molar ratio of 2-methyl-3-butenenitrile to catalyst is generally greater than 1:1, usually in the range from about 5:1 to 20,000:1, preferably 100:1 to 5,000:1, for a batch or continuous operation.

GENERIC EXAMPLES

The invention will now be illustrated by the following non-limiting examples of certain preferred embodiments thereof, wherein all parts, proportions, and percentages are by weight, unless otherwise indicated.

In the following examples, stock solutions of reactants and catalyst were made in the following manner:

1,3-Butadiene Solution (BD): 25 wt % solutions of butadiene were made by vacuum transfer of a known quantity of butadiene into a three-fold amount of toluene. The resulting solutions were stored in a sealed vessel at −35° C. until their use in experiments.

HCN Solution: 25 wt % solutions of HCN were typically made by weighing 2.00 g of liquid HCN into 6.00 g of valeronitrile, in a glovebox. The resulting solutions were stored at −35° C. until their use in experiments.

Catalyst Solution: For a typical multidentate phosphite ligand, 0.84 mmol of P atoms and 0.039 g of Ni(COD)$_2$ (0.14 mmol) were mixed in either toluene or tetrahydrofuran such that the total solution weight would be 5.00 g. The resulting catalyst solutions were typically used immediately after mixing.

2-Methyl-3-butenenitrile Mixture (2M3BN): Samples of 2M3BN were obtained as mixtures of pentenenitrile isomers, which contains 81–82% 2M3BN from Fluka Chemical Corp. (Ronkonkoma, N.Y.) and distilled under nitrogen. Valeronitrile was added as internal standard at the 8 wt % level typically by mixing 0.80 g of valeronitrile and 9.20 g of the distilled 2M3BN.

In the examples as shown in Table 1, the butadiene hydrocyanation experiments were performed as follows. In the Table 1 examples, Examples 1–35 represent examples of the invention while Comparative Examples A–E represent the prior art.

To 4-mL septum-sealed screw-capped vials, 0.064 g of Ni catalyst solution (1.8 μmol Ni), 0.090 g of HCN stock solution (830 μmol HCN), and 0.200 g of BD stock solution (925 μmol BD) were added. The vials were sealed and placed in a hot-block reactor set at 80° C. Samples were removed at the appropriate time points and quenched by cooling to −35° C. The reaction mixtures were then diluted in diethylether (Et$_2$O) as a GC solvent for product analysis as measured against valeronitrile as an internal standard.

In the examples as shown in Table 2, the 2M3BN isomerization experiments were performed as follows. In the Table 2 examples, Examples 36–66 represent examples of the invention while Comparative Examples F–I represent the prior art.

To 4-mL septum-sealed screw-capped vials, 0.070 g of Ni catalyst solution (2.0 μmol Ni) and 0.100 g of the 2M3BN-containing mixture (930 μmol 2M3BN) were added. The vials were sealed and placed in a hot-block reactor set at 125° C. Samples were removed at the appropriate time points and diluted in Et$_2$O for a GC solvent. The valeronltrile was used as an internal standard in the analysis and accounting of the 3PN and 2M3BN reaction product mixture.

TABLE 1

Butadiene Hydrocyanation

| Example | Structure | Time | % 2M3 | % 3PN | Total PN | 3PN/2M3 |
|---|---|---|---|---|---|---|
| A | P(–O–C$_6$H$_4$–Me)$_3$ | 01:30 | 4.1% | 8.0% | 12.1% | 1.98 |
|   |   | 03:00 | 4.9% | 10.0% | 14.9% | 2.04 |
| B | P(–O–C$_6$H$_4$–Me)$_3$ | 01:30 | 2.5% | 4.5% | 7.0% | 1.83 |
|   |   | 03:00 | 3.6% | 6.6% | 10.2% | 1.86 |
| C | P(–O–C$_6$H$_4$–Me)$_3$ | 01:30 | 2.8% | 5.3% | 8.1% | 1.87 |
|   |   | 03:00 | 4.2% | 7.8% | 12.0% | 1.86 |

TABLE 1-continued

Butadiene Hydrocyanation

| Example | Structure | Time | % 2M3 | % 3PN | Total PN | 3PN/2M3 |
|---|---|---|---|---|---|---|
| D | P(–O–C₆H₄–Me)₃ | 1:40 h<br>3:00 h | 3.0%<br>5.3% | 5.5%<br>10.2% | 8.5%<br>15.5% | 1.87<br>1.94 |
| E | P(–O–C₆H₄–Me)₃ | 1:30 hr<br>3:15 hr | 3.6%<br>5.4% | 7.1%<br>11.0% | 10.7%<br>16.4% | 1.95<br>2.05 |
| 1 | (binaphthyl bis-phosphite with 2-ethylphenoxy groups) | 01:30<br>03:00 | 36.6%<br>34.6% | 20.3%<br>22.0% | 56.9%<br>56.6% | 0.56<br>0.64 |
| 2 | (bisphenol ethylidene bridged bis-phosphite, X = P(O-2-ethylphenyl)₂) | 01:30<br>03:00 | 43.7%<br>47.8% | 24.8%<br>26.9% | 68.5%<br>74.6% | 0.57<br>0.56 |
| 3 | (biphenyl bis-phosphite with OMe groups, X = P(O-2,5-dimethylphenyl)₂) | 2:10<br>3:00 | 27.7%<br>17.8% | 37.3%<br>53.4% | 65.0%<br>71.3% | 1.34<br>2.99 |
| 4 | (biphenyl-linked bis-phosphite with propyl tethers) | 1:30<br>3:00 | 39.6%<br>54.6% | 23.3%<br>31.0% | 62.9%<br>85.6% | 0.59<br>0.57 |

TABLE 1-continued
Butadiene Hydrocyanation
| Example | Structure | Time | % 2M3 | % 3PN | Total PN | 3PN/2M3 |
|---|---|---|---|---|---|---|
| 5 | 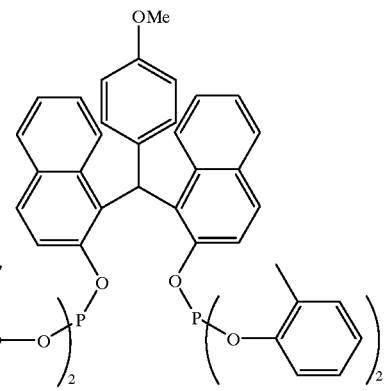 | 1:30<br>3:00 | 31.0%<br>43.4% | 20.4%<br>27.4% | 51.5%<br>70.8% | 0.66<br>0.63 |
| 6 | 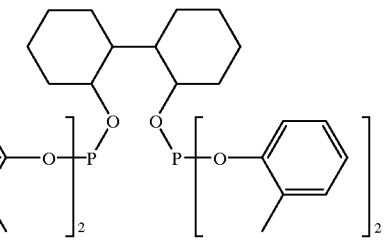 | 01:30<br>03:00 | 20.1%<br>25.1% | 29.2%<br>36.3% | 49.3%<br>61.4% | 1.45<br>1.45 |
| 7 | 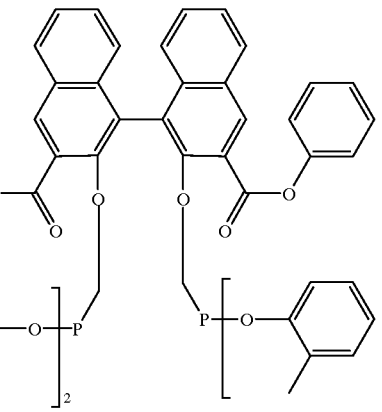 | 01:30<br>03:00 | 36.4%<br>34.9% | 36.4%<br>35.2% | 72.8%<br>70.1% | 1.00<br>1.01 |
| 8 | 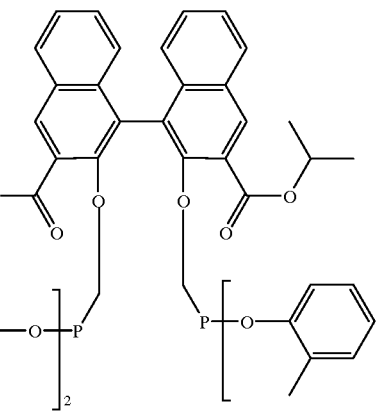 | 01:30<br>03:00 | 35.6%<br>36.7% | 32.1%<br>34.8% | 67.7%<br>71.4% | 0.90<br>0.95 |

TABLE 1-continued

Butadiene Hydrocyanation

| Example | Structure | Time | % 2M3 | % 3PN | Total PN | 3PN/2M3 |
|---------|-----------|------|-------|-------|----------|---------|
| 9 | 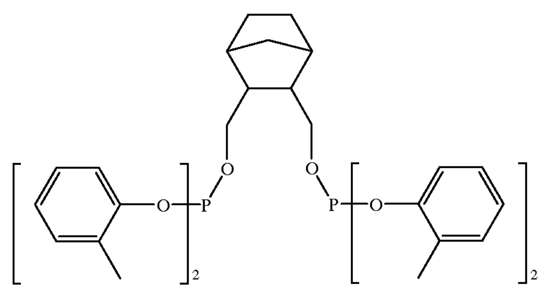 | 01:30 | 8.6% | 13.8% | 22.4% | 1.61 |
|   | | 03:00 | 12.8% | 20.4% | 33.2% | 1.59 |
| 10 | 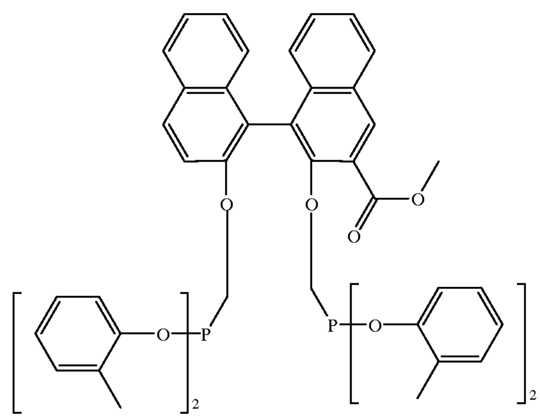 | 01:30 | 48.0% | 34.0% | 81.9% | 0.71 |
|    | | 03:00 | 40.2% | 27.2% | 67.4% | 0.68 |
| 11 | 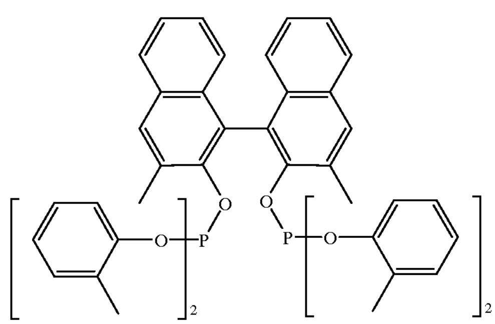 | 01:30 | 15.7% | 48.7% | 64.5% | 3.10 |
|    | | 03:00 | 6.8% | 60.7% | 67.4% | 8.97 |
| 12 | 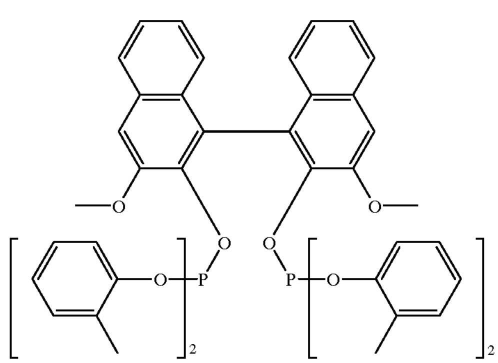 | 01:30 | 43.4% | 39.6% | 83.0% | 0.91 |
|    | | 03:00 | 40.4% | 43.2% | 83.5% | 1.07 |

TABLE 1-continued

Butadiene Hydrocyanation

| Example | Structure | Time | % 2M3 | % 3PN | Total PN | 3PN/2M3 |
|---|---|---|---|---|---|---|
| 13 | 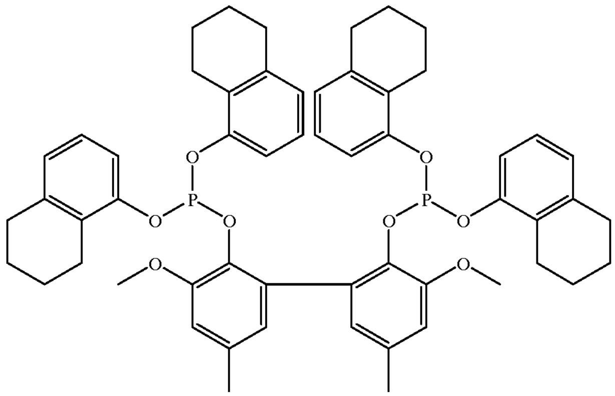 | 01:30 | 34.3% | 43.0% | 77.3% | 1.25 |
| | | 03:10 | 35.6% | 39.3% | 75.0% | 1.10 |
| 14 | 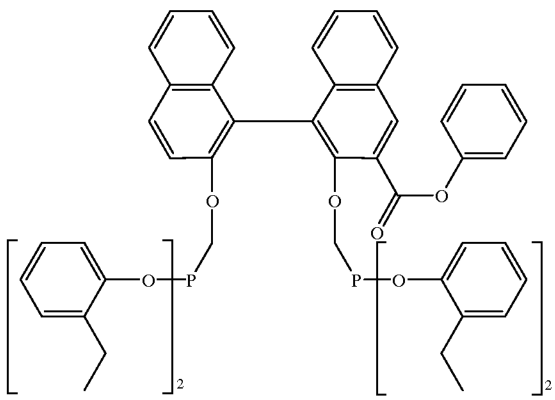 | 1.5 hr | 39.0% | 31.1% | 70.1% | 0.80 |
| | | 3.0 hr | 34.0% | 35.8% | 69.8% | 1.05 |
| 15 | 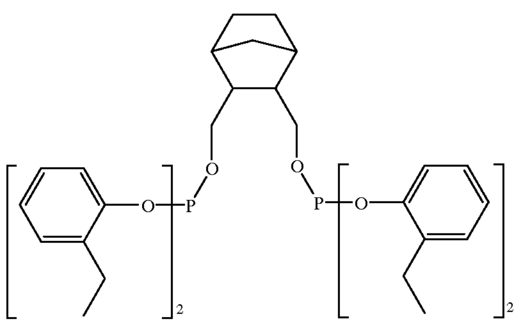 | 1.5 hr | 7.8% | 12.0% | 19.8% | 1.53 |
| | | 3.0 hr | 16.2% | 24.8% | 41.0% | 1.53 |
| 16 | 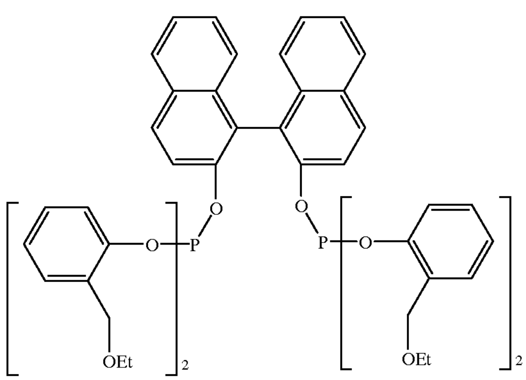 | 1.5 hr | 45.2% | 29.4% | 74.6% | 0.65 |
| | | 3.0 hr | 45.5% | 29.6% | 75.1% | 0.65 |

TABLE 1-continued
Butadiene Hydrocyanation
| Example | Structure | Time | % 2M3 | % 3PN | Total PN | 3PN/2M3 |
|---|---|---|---|---|---|---|
| 17 | 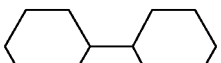 | 1.5 hr<br>3.0 hr | 18.9%<br>22.8% | 23.8%<br>28.5% | 42.7%<br>51.3% | 1.26<br>1.25 |
| 18 | 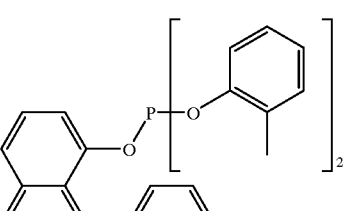 | 1.5 hr<br>3.0 hr | 29.3%<br>27.9% | 38.4%<br>42.0% | 67.7%<br>69.9% | 1.31<br>1.50 |
| 19 | 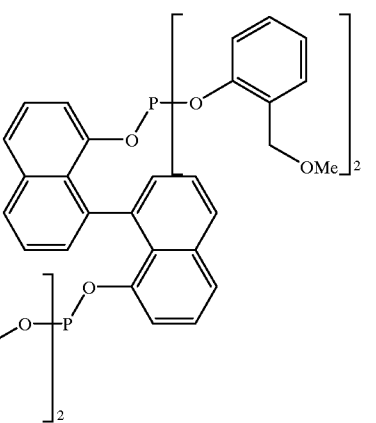 | 1.5 hr<br>3.0 hr | 27.0%<br>27.8% | 36.4%<br>37.3% | 63.4%<br>65.1% | 1.35<br>1.34 |
| 20 | 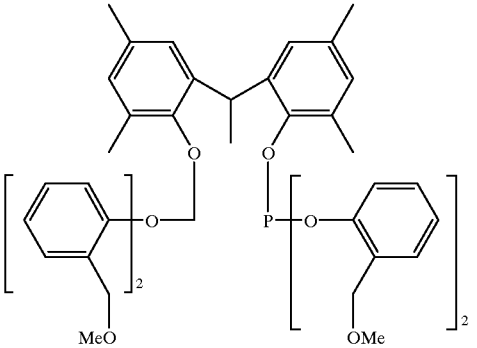 | 1.5 hr<br>3.0 hr | 43.2%<br>43.0% | 30.7%<br>32.6% | 73.8%<br>75.6% | 0.71<br>0.76 |

TABLE 1-continued

Butadiene Hydrocyanation

| Example | Structure | Time | % 2M3 | % 3PN | Total PN | 3PN/2M3 |
|---|---|---|---|---|---|---|
| 21 | 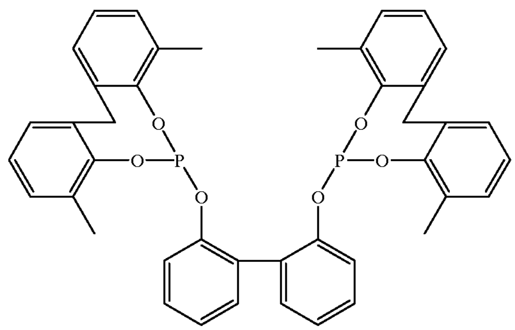 | 1.5 hr | 38.2% | 26.8% | 64.9% | 0.70 |
|    | | 3.0 hr | 38.8% | 27.1% | 65.9% | 0.70 |
| 22 | 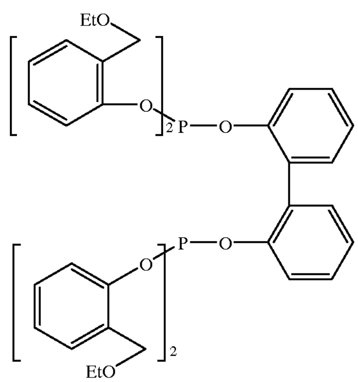 | 1.5 hr | 48.2% | 35.4% | 83.6% | 0.73 |
|    | | 3.0 hr | 47.6% | 35.4% | 82.9% | 0.74 |
| 23 | 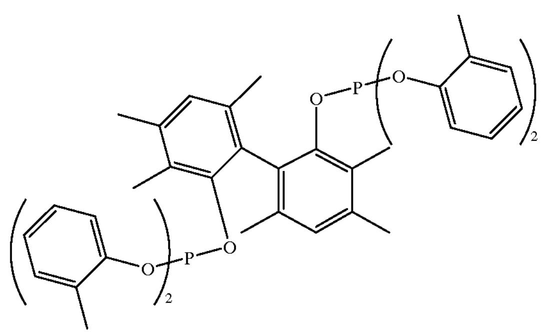 | 1.5 hr | 30.4% | 50.0% | 80.4% | 1.65 |
|    | | 3.0 hr | 18.9% | 59.3% | 78.3% | 3.13 |

TABLE 1-continued
Butadiene Hydrocyanation
| Example | Structure | Time | % 2M3 | % 3PN | Total PN | 3PN/2M3 |
|---|---|---|---|---|---|---|
| 24 | 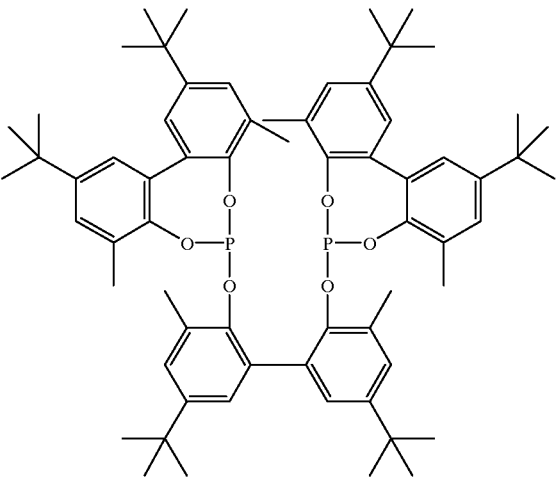 | 1.5 hr<br>3.0 hr | 49.4%<br>53.1% | 13.2%<br>14.2% | 62.6%<br>67.3% | 0.27<br>0.27 |
| 25 | 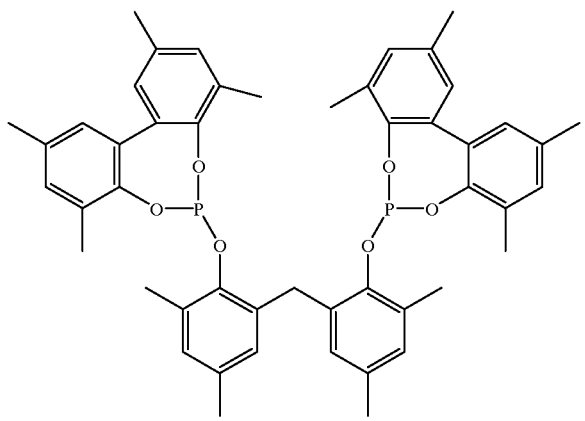 | 1.5 hr<br>3.0 hr | 30.8%<br>31.0% | 37.6%<br>37.8% | 68.4%<br>68.9% | 1.22<br>1.22 |
| 26 | 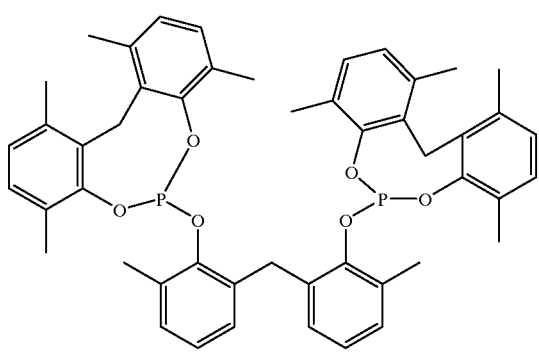 | 1.5 hr<br>3.0 hr | 36.5%<br>34.3% | 47.5%<br>49.8% | 84.0%<br>84.1% | 1.30<br>1.45 |

TABLE 1-continued

Butadiene Hydrocyanation

| Example | Structure | Time | % 2M3 | % 3PN | Total PN | 3PN/2M3 |
|---|---|---|---|---|---|---|
| 27 | 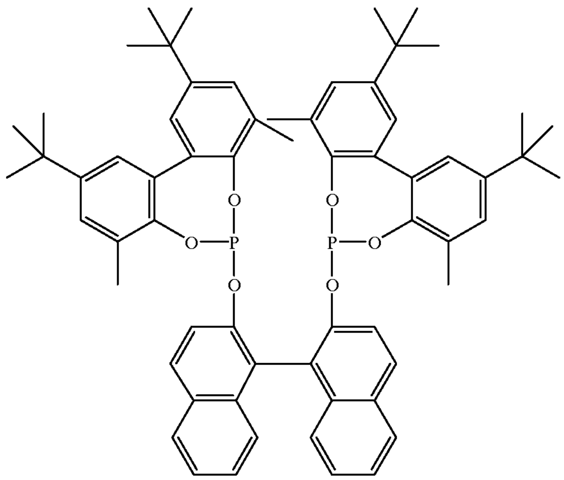 | 1.5 hr | 65.3% | 17.7% | 82.9% | 0.27 |
|    | | 3.0 hr | 64.8% | 17.7% | 82.5% | 0.27 |
| 28 | 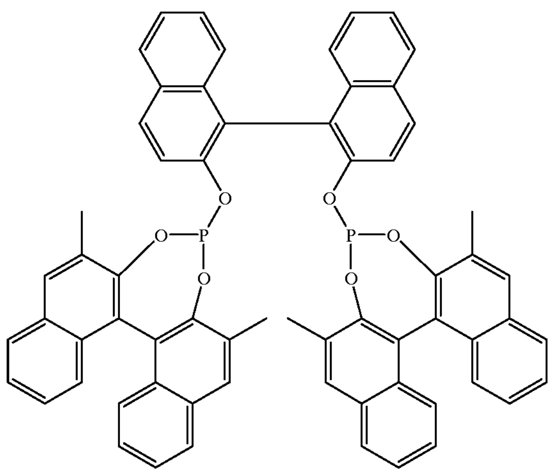 | 1.5 hr | 63.0% | 8.6% | 71.6% | 0.14 |
|    | | 3.0 hr | 66.1% | 9.3% | 75.4% | 0.14 |
| 29 | 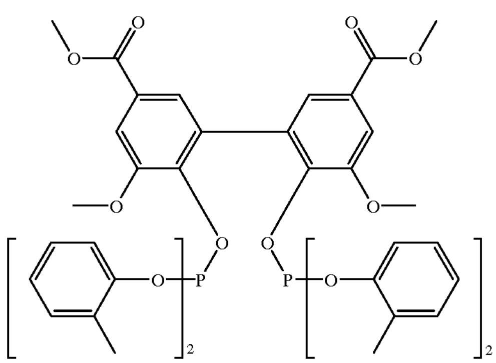 | 1.5 hr | 18.8% | 24.0% | 42.8% | 1.28 |
|    | | 3.0 hr | 28.8% | 37.1% | 65.9% | 1.29 |

TABLE 1-continued
Butadiene Hydrocyanation
| Example | Structure | Time | % 2M3 | % 3PN | Total PN | 3PN/2M3 |
|---|---|---|---|---|---|---|
| 30 | 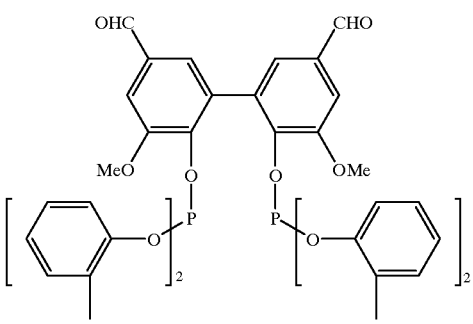 | 1.5 hr<br>3.0 hr | 29.2%<br>30.9% | 39.9%<br>41.9% | 69.1%<br>72.8% | 1.37<br>1.36 |
| 31 | 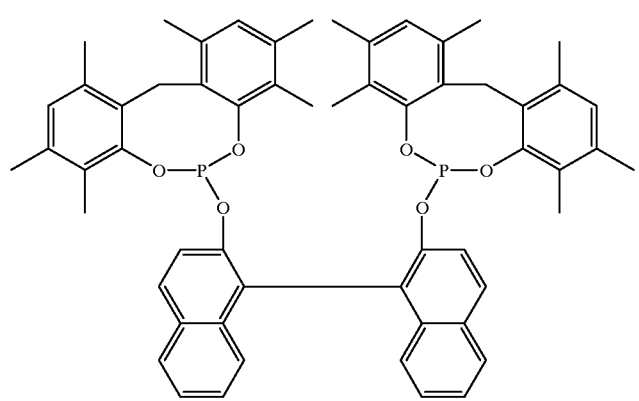 | 1.5 hr<br>3.0 hr | 43.7%<br>39.7% | 26.0%<br>27.7% | 69.7%<br>67.4% | 0.60<br>0.70 |
| 32 | 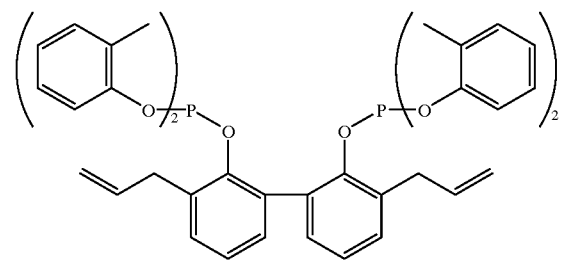 | 1.5 hr<br>3.0 hr | 10.4%<br>12.3% | 16.8%<br>20.0% | 27.2%<br>32.2% | 1.62<br>1.63 |
| 33 | 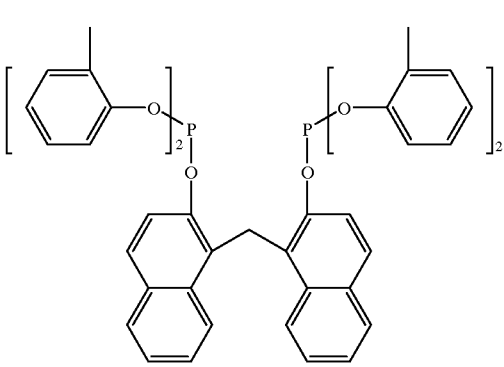 | 1.5 hr<br>3.0 hr | 45.3%<br>44.7% | 35.7%<br>35.6% | 81.0%<br>80.4% | 0.79<br>0.80 |

TABLE 1-continued

Butadiene Hydrocyanation

| Example | Structure | Time | % 2M3 | % 3PN | Total PN | 3PN/2M3 |
|---|---|---|---|---|---|---|
| 34 | 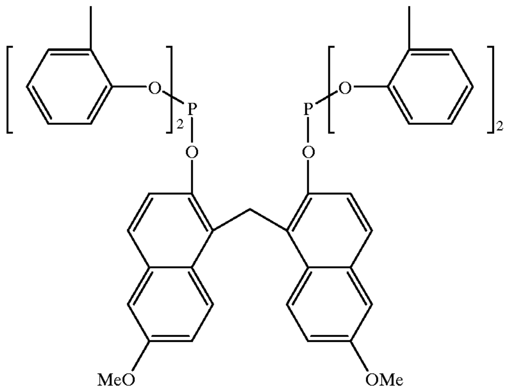 | 1.5 hr | 40.8% | 34.6% | 75.3% | 0.85 |
| | | 3.0 hr | 44.9% | 37.7% | 82.6% | 0.84 |
| 35 | 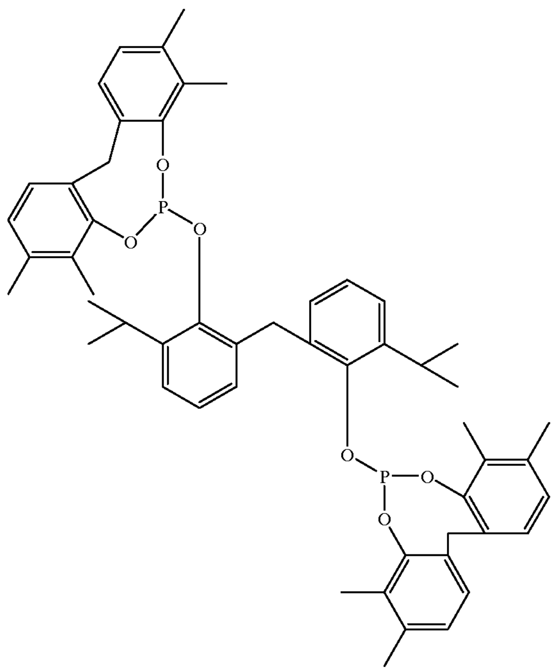 | 1.5 hr | 16.6% | 20.0% | 36.6% | 1.20 |
| | | 3.0 hr | 19.6% | 22.1% | 41.7% | 1.13 |

TABLE 2

Isomization of 2-Methyl-3-Butenenitrile

| Example | Structure | Time | % 2M3 | % 3PN | 3PN/2M3 |
|---|---|---|---|---|---|
| F | 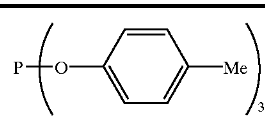 | 01:30 | 81.1% | 20.9% | 0.26 |
| | | 03:00 | 52.3% | 42.8% | 0.82 |
| G | 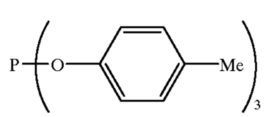 | 01:30 | 89.6% | 10.8% | 0.12 |
| | | 03:00 | 72.3% | 24.7% | 0.34 |

TABLE 2-continued

Isomization of 2-Methyl-3-Butenenitrile

| Example | Structure | Time | % 2M3 | % 3PN | 3PN/2M3 |
|---|---|---|---|---|---|
| H | P(O-C6H4-Me)3 | 01:30<br>03:00 | 78.9%<br>83.9% | 11.9%<br>11.8% | 0.15<br>0.14 |
| I | P(O-C6H4-Me)3 | 1:30<br>3:15 | 90.9%<br>83.7% | 8.3%<br>12.6% | 0.09<br>0.15 |
| 36 | 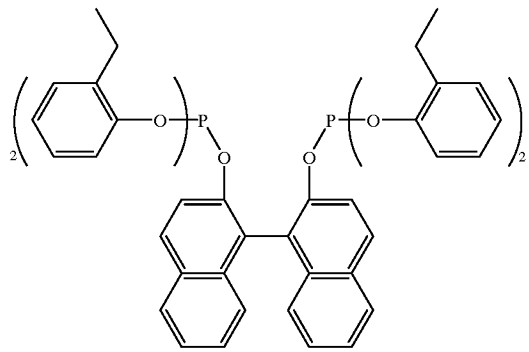 | 01:30<br>03:00 | 7.7%<br>5.9% | 93.0%<br>94.6% | 12.04<br>16.03 |
| 37 | 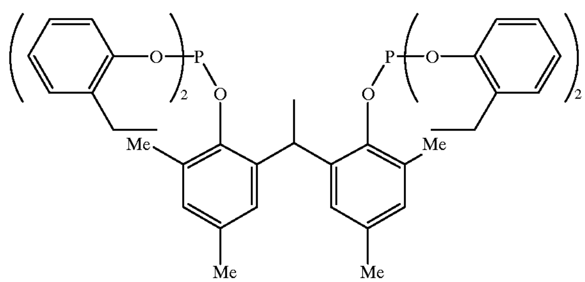 | 01:30<br>03:00 | 25.4%<br>14.2% | 76.0%<br>86.4% | 2.99<br>6.09 |
| 38 | 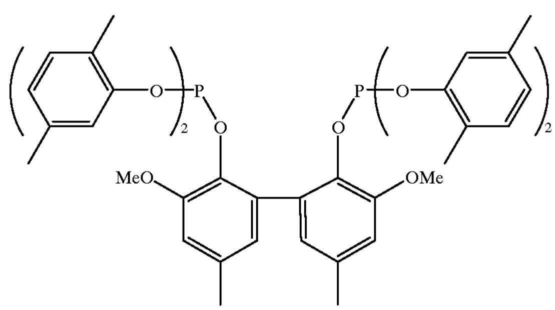 | 2:10 hr<br>3:00 hr | 5.6%<br>5.6% | 94.6%<br>94.6% | 16.96<br>16.85 |
| 39 | 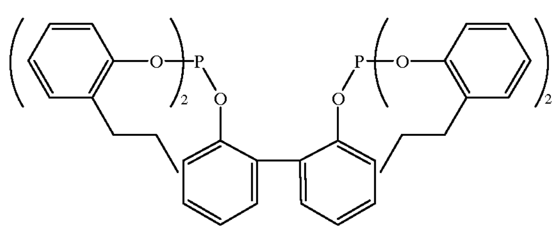 | 1:30 hr<br>3:00 hr | 50.5%<br>15.1% | 48.2%<br>83.9% | 0.96<br>5.56 |

TABLE 2-continued
Isomization of 2-Methyl-3-Butenenitrile
| Example | Structure | Time | % 2M3 | % 3PN | 3PN/2M3 |
|---|---|---|---|---|---|
| 40 | 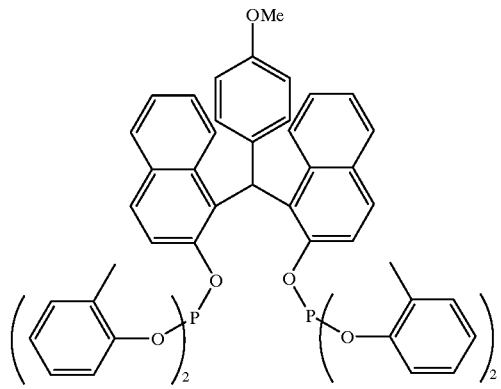 | 1:30 hr<br>3:00 hr | 64.0%<br>43.0% | 34.8%<br>55.2% | 0.54<br>1.28 |
| 41 | 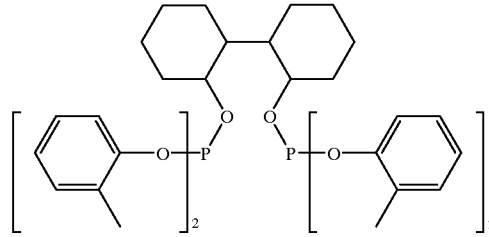 | 01:30<br>03:00 | 6.7%<br>5.3% | 89.2%<br>89.6% | 13.39<br>16.83 |
| 42 | 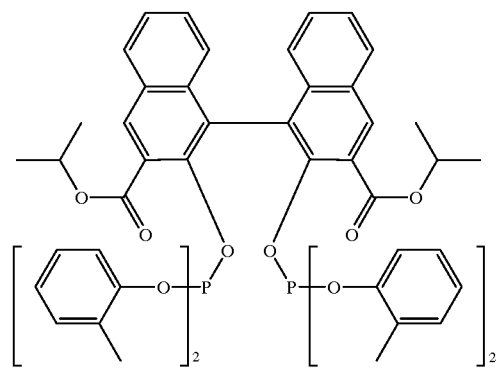 | 01:30<br>03:00 | 24.1%<br>23.9% | 72.2%<br>73.4% | 3.00<br>3.07 |
| 43 | 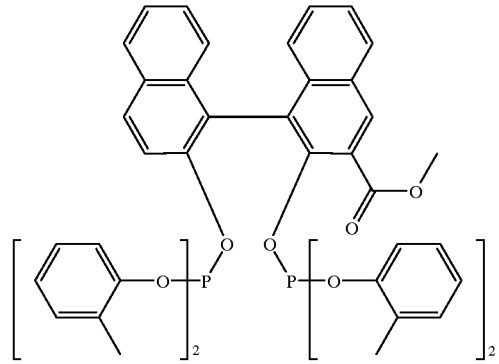 | 01:30<br>03:00 | 8.6%<br>5.8% | 88.4%<br>93.9% | 10.24<br>16.25 |

TABLE 2-continued

Isomization of 2-Methyl-3-Butenenitrile

| Example | Structure | Time | % 2M3 | % 3PN | 3PN/2M3 |
|---|---|---|---|---|---|
| 44 | 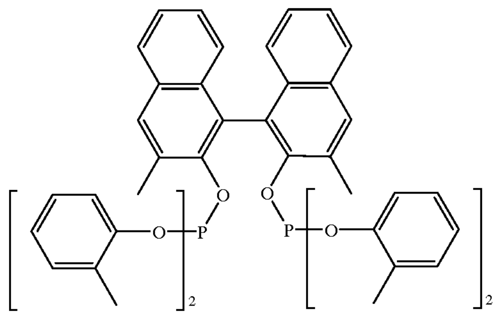 | 01:30 | 5.5% | 94.6% | 17.29 |
| | | 03:00 | 5.4% | 93.4% | 17.23 |
| 45 | 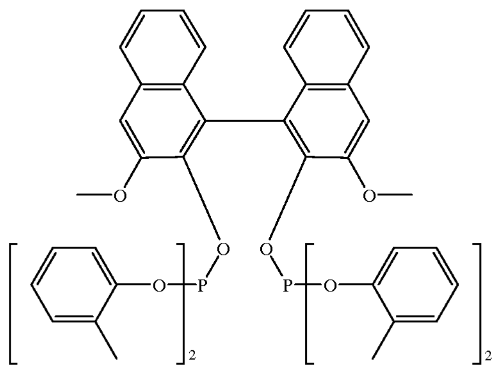 | 01:30 | 5.6% | 94.5% | 16.76 |
| | | 03:00 | 5.7% | 94.4% | 16.71 |
| 46 | 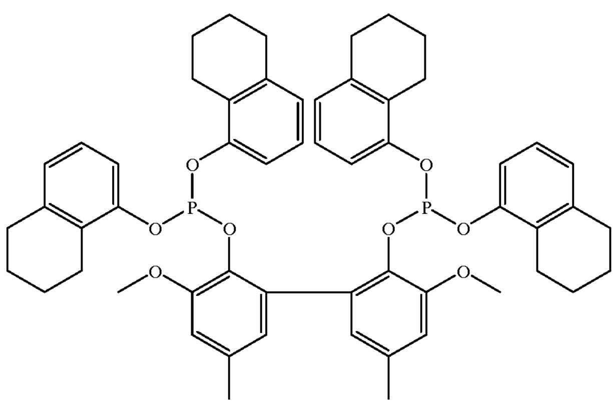 | 01:30 | 5.5% | 93.8% | 16.94 |
| | | 03:10 | 5.0% | 93.9% | 18.67 |
| 47 | 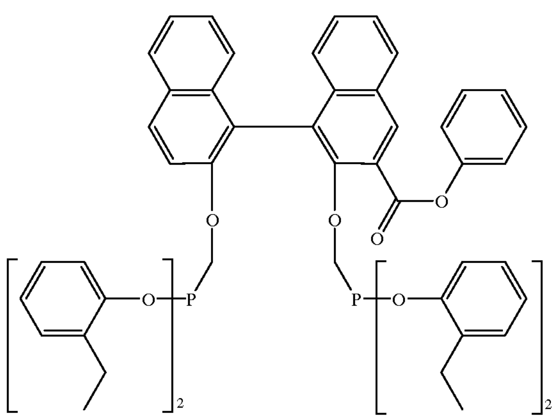 | 1.5 hr | 40.9% | 51.4% | 1.25 |
| | | 3.0 hr | 30.4% | 61.3% | 2.01 |

TABLE 2-continued

Isomization of 2-Methyl-3-Butenenitrile

| Example | Structure | Time | % 2M3 | % 3PN | 3PN/2M3 |
|---------|-----------|------|-------|-------|---------|
| 48 | 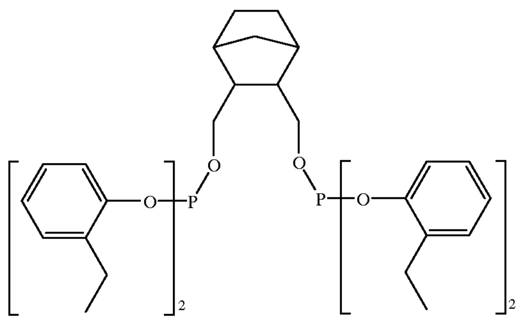 | 1.5 hr | 16.7% | 74.6% | 4.47 |
|    | | 3.0 hr | 6.3%  | 82.7% | 13.21 |
| 49 | 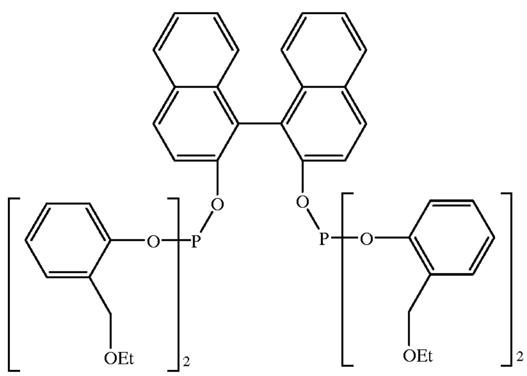 | 1.5 hr | 36.6% | 60.8% | 1.66 |
|    | | 3.0 hr | 14.4% | 81.8% | 5.69 |
| 50 | 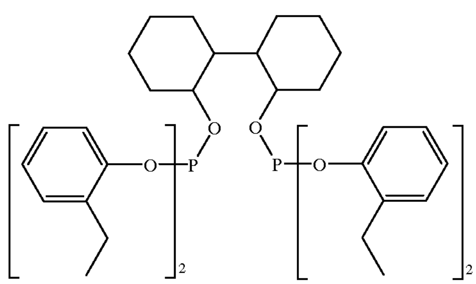 | 1.5 hr | 5.5%  | 89.4% | 16.19 |
|    | | 3.0 hr | 5.2%  | 89.4% | 17.10 |
| 51 | 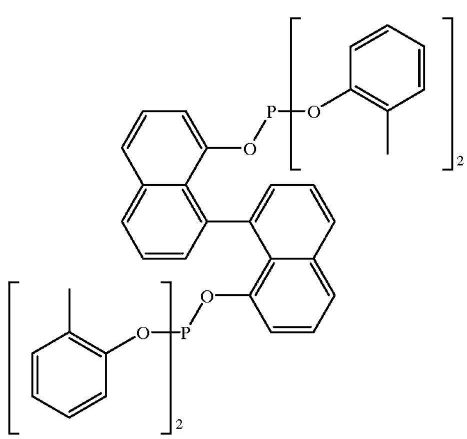 | 1.5 hr | 5.4%  | 91.7% | 17.12 |
|    | | 3.0 hr | 5.7%  | 91.2% | 16.08 |

TABLE 2-continued

Isomization of 2-Methyl-3-Butenenitrile

| Example | Structure | Time | % 2M3 | % 3PN | 3PN/2M3 |
|---|---|---|---|---|---|
| 52 | 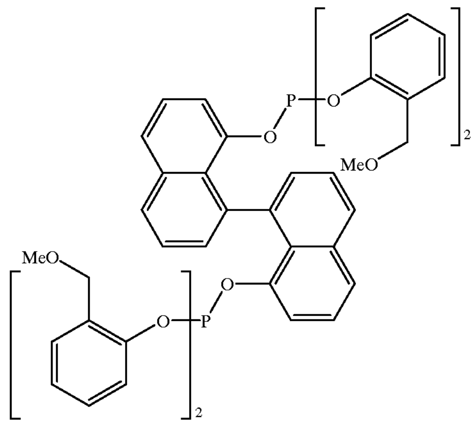 | 1.5 hr<br>3.0 hr | 5.4%<br>5.2% | 90.5%<br>90.2% | 16.84<br>17.30 |
| 53 | 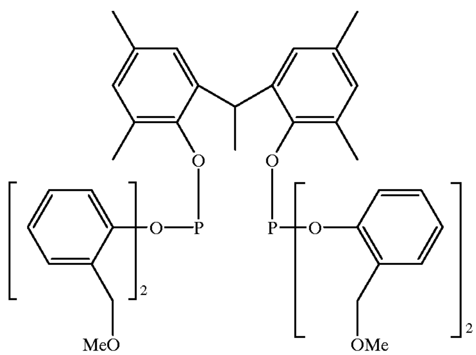 | 1.5 hr<br>3.0 hr | 7.0%<br>5.8% | 91.1%<br>91.1% | 13.05<br>15.73 |
| 54 | 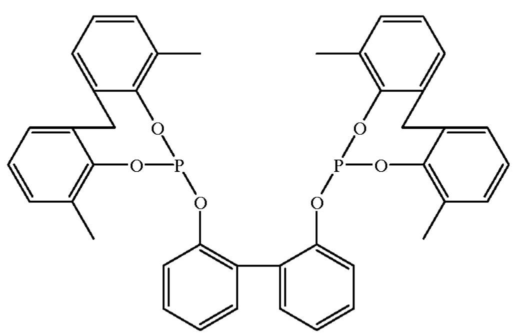 | 1.5 hr<br>3.0 hr | 9.9%<br>5.8% | 88.6%<br>92.3% | 8.92<br>15.93 |
| 55 | 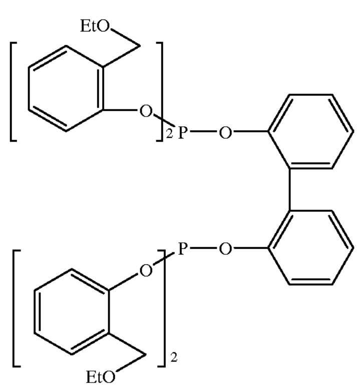 | 1.5 hr<br>3.0 hr | 16.8%<br>9.0% | 81.3%<br>87.9% | 4.84<br>9.75 |

TABLE 2-continued

Isomization of 2-Methyl-3-Butenenitrile

| Example | Structure | Time | % 2M3 | % 3PN | 3PN/2M3 |
|---|---|---|---|---|---|
| 56 | 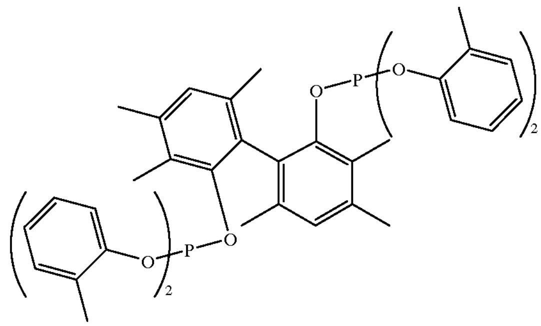 | 1.5 hr | 5.5% | 92.2% | 16.86 |
|    | | 3.0 hr | 5.3% | 92.7% | 17.49 |
| 57 | 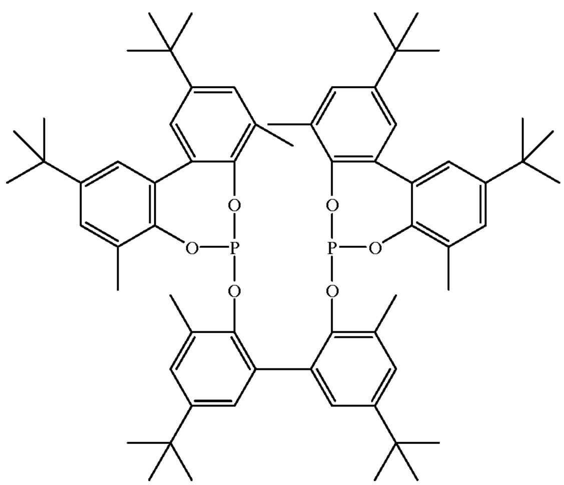 | 1.5 hr | 20.7% | 79.7% | 3.86 |
|    | | 3.0 hr | 9.9% | 90.0% | 9.13 |
| 58 | 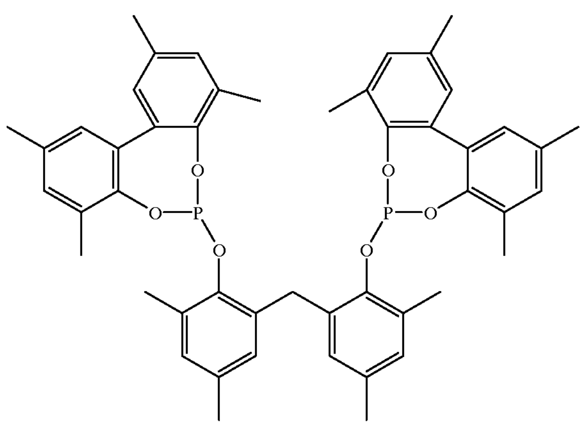 | 1.5 hr | 7.7% | 90.2% | 11.73 |
|    | | 3.0 hr | 5.1% | 91.9% | 17.93 |

TABLE 2-continued

Isomization of 2-Methyl-3-Butenenitrile

| Example | Structure | Time | % 2M3 | % 3PN | 3PN/2M3 |
|---|---|---|---|---|---|
| 59 | 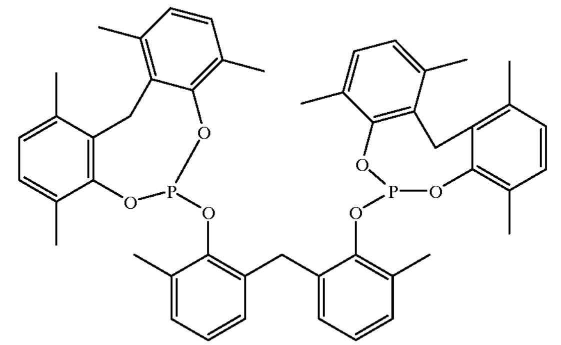 | 1.5 hr | 9.7% | 89.1% | 9.17 |
|  | | 3.0 hr | 5.7% | 93.1% | 16.26 |
| 60 | 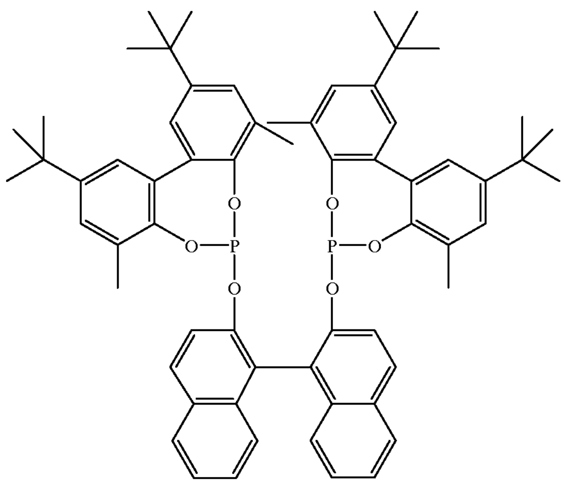 | 1.5 hr | 57.7% | 39.3% | 0.68 |
|  | | 3.0 hr | 32.3% | 65.2% | 2.02 |
| 61 | 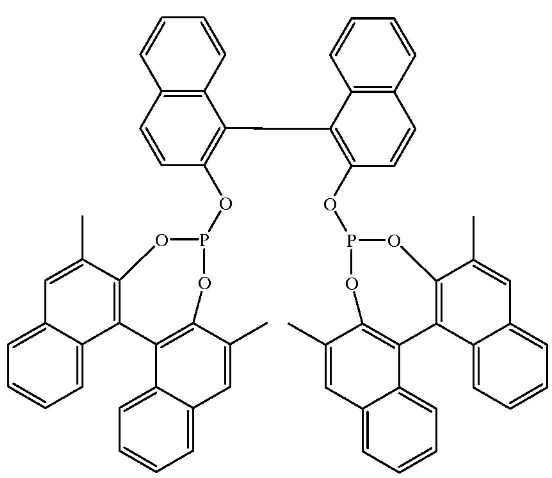 | 1.5 hr | 50.5% | 47.1% | 0.93 |
|  | | 3.0 hr | 28.6% | 69.2% | 2.42 |

TABLE 2-continued

Isomization of 2-Methyl-3-Butenenitrile

| Example | Structure | Time | % 2M3 | % 3PN | 3PN/2M3 |
|---|---|---|---|---|---|
| 62 | 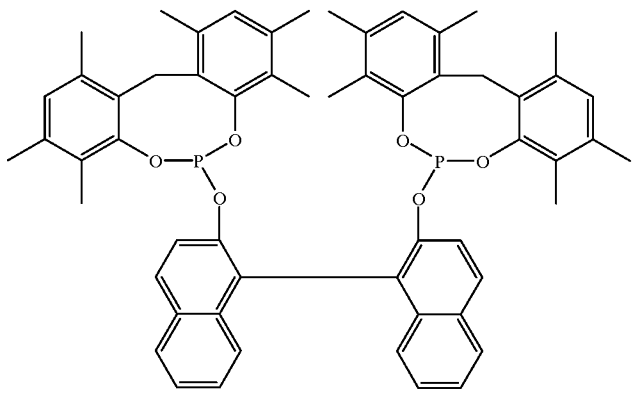 | 1.5 hr | 18.5% | 80.9% | 4.39 |
| | | 3.0 hr | 5.7% | 93.6% | 16.53 |
| 63 | 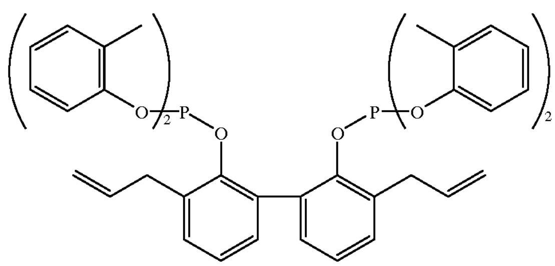 | 1.5 hr | 11.0% | 87.7% | 7.99 |
| | | 3.0 hr | 6.2% | 91.7% | 14.73 |
| 64 | 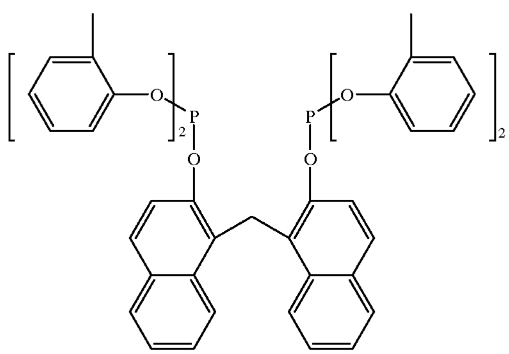 | 1.5 hr | 70.7% | 28.2% | 0.40 |
| | | 3.0 hr | 47.6% | 51.5% | 1.08 |
| 65 | 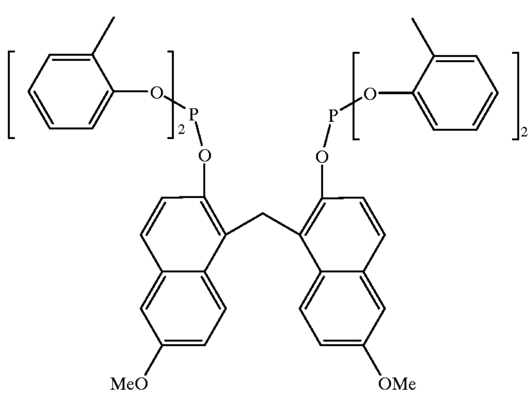 | 1.5 hr | 54.2% | 45.3% | 0.84 |
| | | 3.0 hr | 37.3% | 62.3% | 1.67 |

TABLE 2-continued

Isomization of 2-Methyl-3-Butenenitrile

| Example | Structure | Time | % 2M3 | % 3PN | 3PN/2M3 |
|---------|-----------|------|-------|-------|---------|
| 66 | 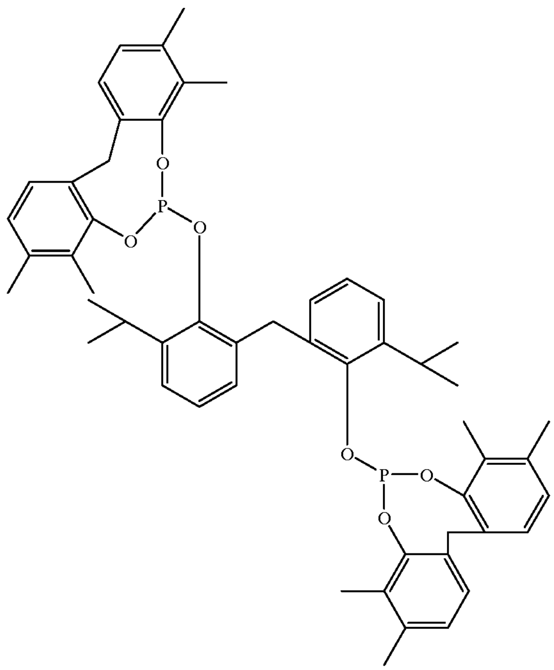 | 1.5 hr | 10.4% | 87.5% | 8.44 |
|    | | 3.0 hr | 11.1% | 86.5% | 7.80 |

Although particular embodiments of the present invention have been described in the foregoing description, it will be understood by those skilled in the art that the invention is capable of numerous modifications, substitutions and rearrangements without departing from the spirit or essential attributes of the invention. Reference should be made to the appended claims, rather than to the foregoing specification, as indicating the scope of the invention.

What is claimed is:

1. A multidentate phosphite ligand selected from the group consisting of Formulas X, XI XII, XIII and XIV as set forth below:

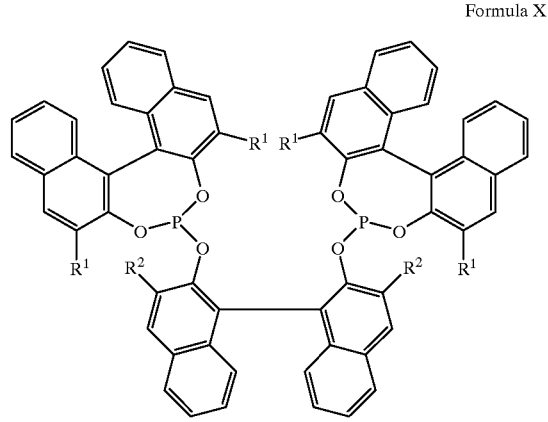

Formula X

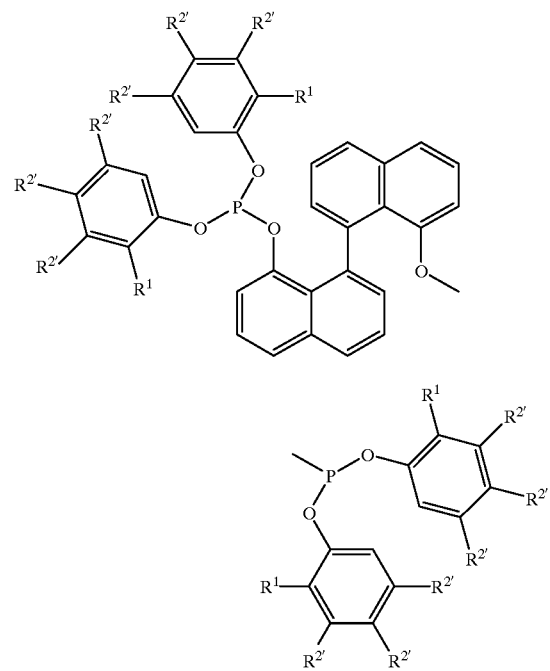

-continued

Formula XI

Formula XII

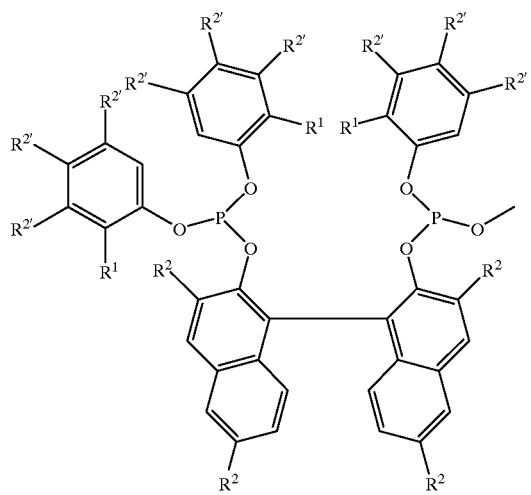

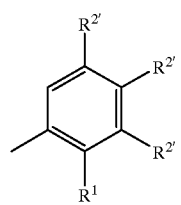

Formula XIII

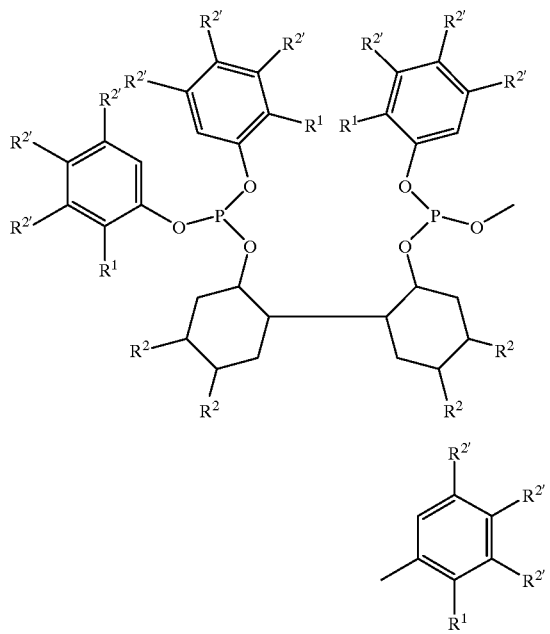

Formula XIV

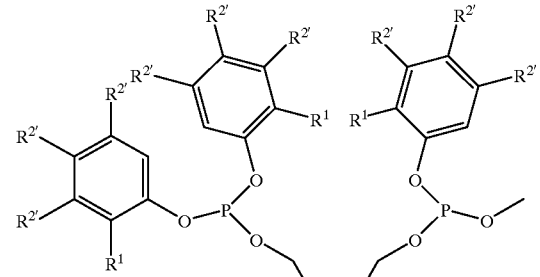

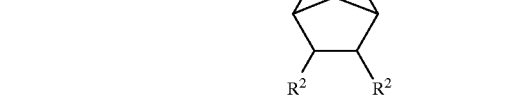

wherein each $R^1$ is independently a primary, secondary, or tertiary hydrocarbyl of 1 to 12 carbon atoms or $CH_2OR^3$ wherein $R^3$ is a $C_1$ to $C_{12}$ alkyl; with the proviso that at least one of $R^1$ must be a primary hydrocarbyl or $CH_2OR^3$;

each $R^2$ is independently H, halogen, primary or secondary hydrocarbyl of 1 to 12 carbon atoms, $OR^3$ wherein $R^3$ is a $C_1$ to $C_{12}$ alkyl, or $CO_2R^{3'}$ wherein $R^{3'}$ is an aryl or a $C_1$ to $C_{12}$ alkyl; and each $R^{2'}$ is independently H, halogen, CHO, primary, secondary or tertiary hydrocarbyl of 1 to 12 carbon atoms, $OR^3$ wherein $R^3$ is a $C_1$ to $C_{12}$ alkyl, $CO_2R^{3'}$ wherein $R^{3'}$ is an aryl or a $C_1$ to $C_{12}$ alkyl, or $C(R^3)(O)$ wherein $R^3$ is a $C_1$ to $C_{12}$ alkyl.

2. A catalyst precursor composition comprising zero-valent nickel and a multidentate phosphite ligand according to claim 1.

* * * * *

UNITED STATES PATENT AND TRADEMARK OFFICE
CERTIFICATE OF CORRECTION

PATENT NO : 6,120,700

DATED : September 19, 2000

INVENTOR(S) : Thomas Foo, et al.

It is certified that error appears in the above-identified patent and that said Letters Patent is hereby corrected as shown below:

IN THE ABSTRACT

In line 4, after the word the, please delete the word "nitrites" and insert the word -- nitriles --

IN THE SPECIFICATION

In column 1, line 13, after the word acyclic, please delete the word "nitrites" and insert the word -- nitriles -- thereof.

In column 1, line 15, after the word linear, please delete the word "nitrites" and insert the word -- nitriles -- thereof.

In column 2, line 22, please delete the word "nitrites" and insert the word -- nitriles -- thereof.

In column 2, line 33, please delete the word "nitrites" and insert the word -- nitriles -- thereof.

In column 21, line 30, after the word wherein, please delete the "R3'" and insert -- R3' -- thereof.

In column 21, line 40, after the word each, please delete the word "R4'" and insert -- R4' -- thereof.

After columns 25 and 26, Table 1, in the header, please delete "2M3", which appears twice in each header through columns 45 and 46, and insert -- 2M3BN -- throughout.

After columns 45 and 46, Table 2, in the header, please delete "2M3", which appears twice in each header through columns 63 and 64, and insert -- 2M3BN -- throughout.

Examples 7, 8, 10, 14 in Table 1 should be single bonds P-O in structure

UNITED STATES PATENT AND TRADEMARK OFFICE
CERTIFICATE OF CORRECTION

PATENT NO : 6,120,700

DATED : September 19, 2000

INVENTOR(S) : Thomas Foo, et al.

It is certified that error appears in the above-identified patent and that said Letters Patent is hereby corrected as shown below:

In column 29, Table 1, Example 7, replace the existing structure with the following:

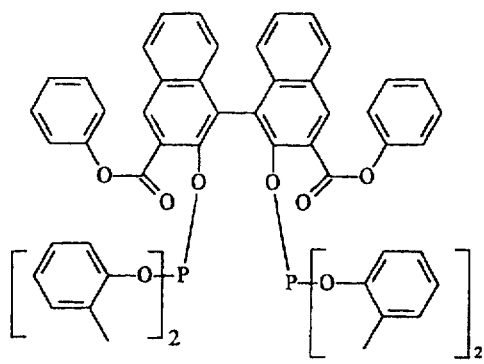

UNITED STATES PATENT AND TRADEMARK OFFICE
CERTIFICATE OF CORRECTION

PATENT NO : 6,120,700

DATED : September 19, 2000

INVENTOR(S) : Thomas Foo, et al.

It is certified that error appears in the above-identified patent and that said Letters Patent is hereby corrected as shown below:

In column 29, Table 1, Example 8, replace the existing structure with the following:

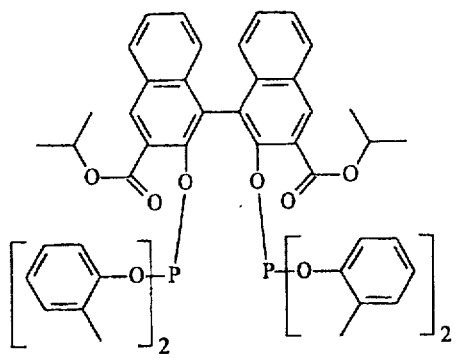

UNITED STATES PATENT AND TRADEMARK OFFICE
CERTIFICATE OF CORRECTION

PATENT NO : 6,120,700

DATED : September 19, 2000

INVENTOR(S) : Thomas Foo, et al.

It is certified that error appears in the above-identified patent and that said Letters Patent is hereby corrected as shown below:

IN THE CLAIMS:
In column 64, replace Formula XI with the following:

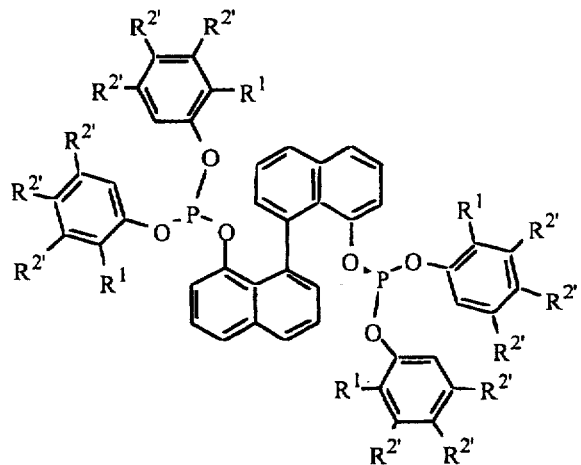

UNITED STATES PATENT AND TRADEMARK OFFICE
CERTIFICATE OF CORRECTION

PATENT NO : 6,120,700

DATED : September 19, 2000

INVENTOR(S) : Thomas Foo, et al.

It is certified that error appears in the above-identified patent and that said Letters Patent is hereby corrected as shown below:

In column 65, replace Formula XII with the following:

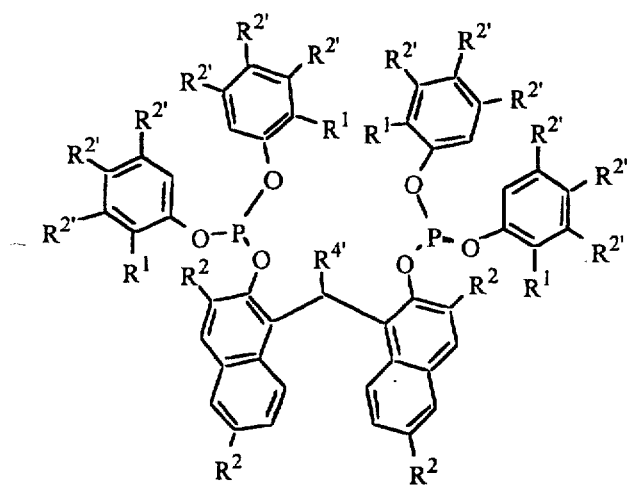

UNITED STATES PATENT AND TRADEMARK OFFICE
CERTIFICATE OF CORRECTION

PATENT NO : 6,120,700

DATED : September 19, 2000

INVENTOR(S) : Thomas Foo, et al.

It is certified that error appears in the above-identified patent and that said Letters Patent is hereby corrected as shown below:

In column 31, Table 1, Example 10, replace the existing structure with the following:

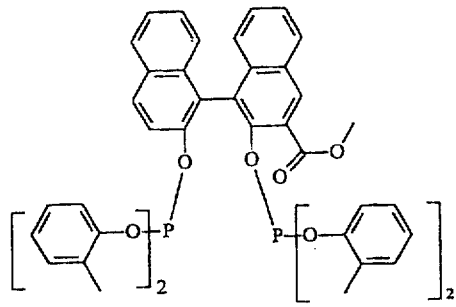

UNITED STATES PATENT AND TRADEMARK OFFICE
CERTIFICATE OF CORRECTION

PATENT NO : 6,120,700

DATED : September 19, 2000

INVENTOR(S) : Thomas Foo, et al.

It is certified that error appears in the above-identified patent and that said Letters Patent is hereby corrected as shown below:

In column 33, Table 1, Example 14, replace the existing structure with the following:

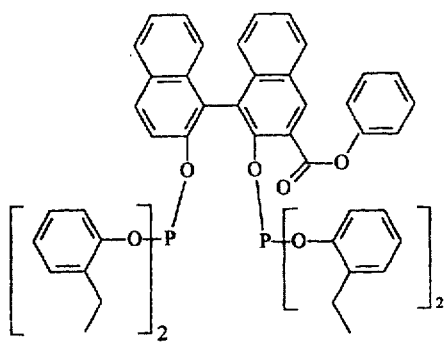

UNITED STATES PATENT AND TRADEMARK OFFICE
CERTIFICATE OF CORRECTION

PATENT NO : 6,120,700

DATED : September 19, 2000

INVENTOR(S) : Thomas Foo, et al.

It is certified that error appears in the above-identified patent and that said Letters Patent is hereby corrected as shown below:

In column 51, Table 2, Example 47, replace the existing structure with the following:

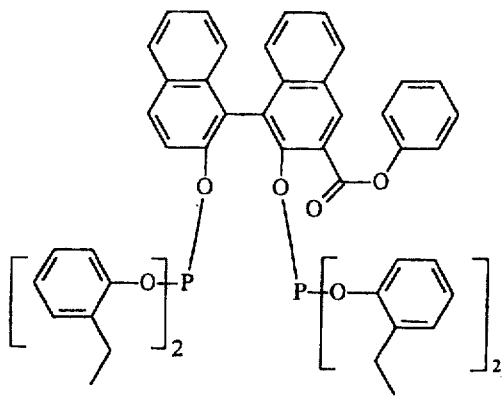

UNITED STATES PATENT AND TRADEMARK OFFICE
CERTIFICATE OF CORRECTION

PATENT NO : 6,120,700

DATED : September 19, 2000

INVENTOR(S) : Thomas Foo, et al.

It is certified that error appears in the above-identified patent and that said Letters Patent is hereby corrected as shown below:

In column 66, replace Formula XIV with the following:

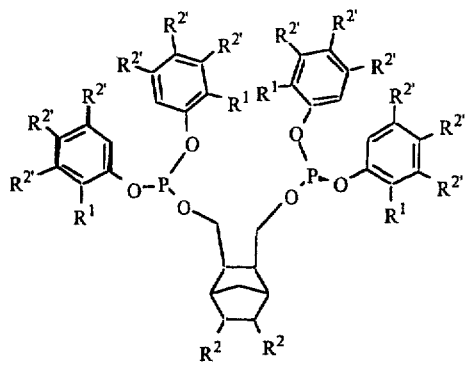

Signed and Sealed this

Twenty-ninth Day of May, 2001

Attest:

NICHOLAS P. GODICI

Attesting Officer   Acting Director of the United States Patent and Trademark Office